United States Patent
Ito et al.

(10) Patent No.: US 6,271,385 B1
(45) Date of Patent: Aug. 7, 2001

(54) N-HETEROCYCLIC METHYLPROPYLAMINE DERIVATIVES, PROCESS FOR PRODUCING THE SAME AND GERMICIDES

(75) Inventors: Atsushi Ito; Satoru Kumazawa; Keiichi Sudo, all of Iwaki; Tsumoru Watanabe, Kitaibaraki; Takayoshi Eizuka; Yoshitaka Niizeki, both of Iwaki, all of (JP)

(73) Assignee: Kureha Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/508,347

(22) PCT Filed: Sep. 11, 1998

(86) PCT No.: PCT/JP98/04117

§ 371 Date: Mar. 10, 2000

§ 102(e) Date: Mar. 10, 2000

(87) PCT Pub. No.: WO99/12902

PCT Pub. Date: Mar. 18, 1999

(30) Foreign Application Priority Data

Sep. 11, 1997 (JP) ................................... 9-246906

(51) Int. Cl.⁷ .................. A01N 57/18; C07D 241/02; C07D 211/70; C07D 277/20; C07D 261/14

(52) U.S. Cl. .................. 546/329; 544/336; 548/202; 548/235; 548/335.5; 548/561; 504/205; 504/244; 504/266; 504/270; 504/275; 504/284

(58) Field of Search ................... 504/205, 244, 504/266, 270, 275, 284; 544/336; 546/329; 548/202, 235, 335.5, 561

(56) References Cited

PUBLICATIONS

Lutz, Gary P., J Org Chem, vol 61, pp 4542–4544, 1996.*

* cited by examiner

Primary Examiner—D. Margaret Seaman
(74) Attorney, Agent, or Firm—Beyer Weaver & Thomas, LLP

(57) ABSTRACT

N-heterocyclicmethylpropylamine derivatives of formula (I):

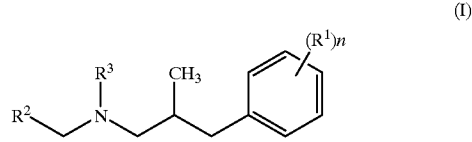

and acid addition salts thereof;

wherein $R^1$ represents hydrogen, halogen, alkyl, alkenyl, halogenated alkyl, alkoxy, halogenated alkoxy, hydroxyl, cyano, nitro, phenyl optionally having a substituent on a ring thereof or phenoxy; n represents an integer of 0–5; $R^2$ represents a heterocycle containing at least one nitrogen atom as the hetero atom and optionally having a substituent on a ring thereof; and $R^3$ represents hydrogen or $C_1$–$C_5$ alkyl.

2 Claims, No Drawings

N-HETEROCYCLIC METHYLPROPYLAMINE DERIVATIVES, PROCESS FOR PRODUCING THE SAME AND GERMICIDES

TECHNICAL FIELD

This invention relates to novel propylamine derivatives having physiological activities, and particularly it relates to novel N-heterocyclicmethylpropylamine derivatives that can be utilized as the effective ingredients of fungicides (such as those for use in farming and horticulture).

BACKGROUND ART

Commercially available fungicides include, as 3-phenylpropylamines, N-[3-p-t-butylphenyl-2-methyl-1-propyl]-cis-2,6-dimethylmorpholine (fenpropimorph), a compound described in Japanese Unexamined Patent Publication No. SHO 53-77070, and N-[3-p-t-butylphenyl-2-methyl-1-propyl]piperidine (fenpropidine), a compound described in Japanese Unexamined Patent Publication No. SHO 53-68785 and No. SHO 53-68786.

The nitrogen atom of the amino group in each of the aforementioned compounds forms part of a ring. In contrast, the only compounds known wherein the nitrogen atom of the amino group does not form part of a ring and a heterocyclicmethyl group is bonded to the nitrogen atom, are those with a tetrahydrofurfuryl group as described in Japanese Unexamined Patent Publication No. SHO 63-258867, those with heterocyclicmethyl groups containing oxygen or sulfur, such as thenyl, and the following compounds listed in Pestic. Sci., 35, 339 (1992):

N-[3-(4-t-butylphenyl)-2-methylpropyl]-N-(t-butyl)-3-pyridylmethylamine;
N-[3-(4-t-butylphenyl)-2-methylpropyl]-N-butyl-3-pyridylmethylamine; and
N-[3-(4-t-butylphenyl)-2-methylpropyl]-N-methyl-3-pyridylmethylamine.

DISCLOSURE OF THE INVENTION

However, except for the aforementioned compounds having a 3-pyridylmethyl group, no compounds are known wherein a heterocycle containing at least one nitrogen atom as the hetero atom and having an optional substituent on the ring is bonded to the nitrogen atom of the amino group via methylene, such as in the N-heterocyclicmethylpropylamine derivatives represented by the following formula (I):

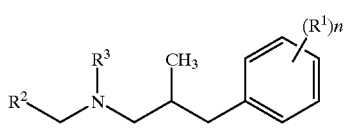

(I)

Moreover, no compounds with substituents on the heterocycle have yet been reported, and consequently no studies have yet been conducted on the usefulness of such compounds.

It is an object of this invention to provide a novel N-heterocyclicmethylpropylamine derivative that is useful as a physiologically active substance in a fungicide, for example. It is another object of the invention to provide a process for preparation of the N-heterocyclicmethylpropylamine derivatives described above and utility therefor.

According to this invention, there is provided a N-heterocyclicmethylpropylamine derivative of formula (I):

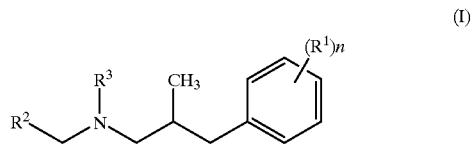

(I)

or an acid addition salt thereof;

wherein $R^1$ represents at least one moiety selected from the group consisting of hydrogen, halogen, $C_1$–$C_6$ alkyl, $C_1$–$C_6$ alkenyl, $C_1$–$C_6$ halogenated alkyl, $C_1$–$C_6$ alkoxy, $C_1$–$C_6$ halogenated alkoxy, hydroxyl, cyano, nitro, phenyl optionally having a substituent on a ring thereof and phenoxy; n represents an integer of 0–5; when n is 2 or greater, each $R^1$ may be the same or different and two $R^1$ groups may be bonded together into a ring or crosslinked; $R^2$ represents a heterocycle containing at least one nitrogen atom as the hetero atom and optionally having a substituent on a ring thereof; and $R^3$ represents at least one moiety selected from the group consisting of hydrogen and $C_1$–$C_5$ alkyl, with the proviso that the following compounds are excluded:

N-[3-(4-t-butylphenyl)-2-methylpropyl]-N-(t-butyl)-3-pyridylmethylamine,
N-[3-(4-t-butylphenyl)-2-methylpropyl]-N-butyl-3-pyridylmethylamine, and
N-[3-(4-t-butylphenyl)-2-methylpropyl]-N-methyl-3-pyridylmethylamine.

Optical isomers may exist for the N-heterocyclicmethylpropylamine derivative of formula (I) of the invention as described above, because there is an asymmetric carbon at the 2-position of its propyl group, regardless of any asymmetry due to other substituents. Consequently, a compound of formula (I) of the invention naturally encompasses either of single optical isomers and any mixtures of the optical isomers.

According to the invention, there is also provided a process for preparation comprising reductive amination between a 3-phenylpropionaldehyde derivative of formula (II) and a heterocyclicmethylamine derivative of formula (III) to obtain an N-heterocyclicmethylpropylamine derivative of formula (I):

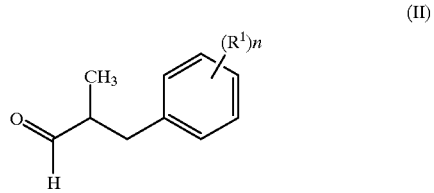

(II)

(III)

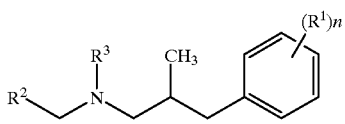

(in formulae (I), (II) and (III) $R^1$, $R^2$, $R^3$ and n are as previously defined).

According to the invention, reductive amination may be employed to synthesize a 3-phenylpropylamine derivative of formula (IV) from a 3-phenylpropionaldehyde derivative of formula (II) and an aminating agent of formula (VIII) or, alternatively, a 3-phenylpropionamide derivative of formula (XII) may be reduced to synthesize a 3-phenylpropylamine derivative of formula (IV); and an N-heterocyclicmethylpropylamine derivative of formula (I) is synthesized from this compound (IV) and a heterocyclemethylating agent of formula (V). On the other hand, reductive amination may also be used to synthesize an N-heterocyclicmethylpropylamine derivative of formula (I) from a compound of (IV) and a heterocyclicaldehyde derivative of formula (VI):

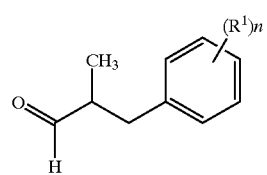

$R^3NH_2$ (VIII)

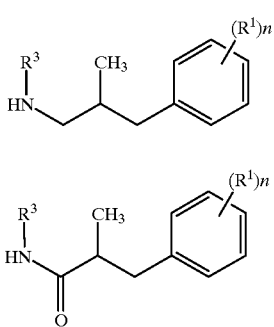

$R^2CH_2X$ (V)

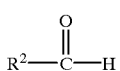

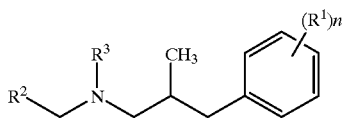

(in the above formulae $R^1$, $R^2$, $R^3$ and n are as previously defined, and X represents a leaving group).

BEST MODE FOR CARRYING OUT THE INVENTION

This invention will be explained in greater detail hereinbelow.

N-heterocyclicmethylpropylamine Derivatives

In the N-heterocyclicmethylpropylamine derivatives of formula (I) above, $R^1$ represents at least one moiety selected from the group consisting of hydrogen, halogen, $C_1-C_6$ alkyl, $C_1-C_6$ alkenyl, $C_1-C_6$ halogenated alkyl, $C_1-C_6$ alkoxy, $C_1-C_6$ halogenated alkoxy, hydroxyl, cyano, nitro, phenyl optionally having a substituent on a ring thereof, and phenoxy. The halogen atom may be fluorine, chlorine, bromine or iodine. The alkyl portion of the $C_1-C_6$ alkyl, $C_1-C_6$ halogenated alkyl, $C_1-C_6$ alkoxy or $C_1-C_6$ halogenated alkoxy group may be primary, secondary or tertiary.

Among these groups for $R^1$ preferred are halogen atoms, halogenated alkyl, halogenated alkoxy and tertiary alkyl groups, examples of which include chlorine, fluorine and bromine atoms, and trifluoromethyl, trifluoromethoxy and 1,1-dimethylethyl (equivalent to t-butyl) groups. The position of substitution on the phenyl ring of $R^1$ is not particularly limited, but the 3-position and 4-position are preferred.

"n" represents an integer of 0–5, and n is preferably 1 or 2. When n is 2 or greater, each $R^1$ may be the same or different. Also, two $R^1$ groups may be bonded together into a ring or crosslinked, and for example, they may together with the benzene ring form indane, 1,2-methylenedioxybenzene or naphthalene.

$R^2$ represents a heterocycle containing at least one nitrogen atom as the hetero atom and optionally having a substituent on a ring thereof. This heterocycle $R^2$ contains at least one nitrogen atom as the hetero atom, although it may also have one or more other hetero atoms (oxygen, sulfur, etc.), and the heterocycle $R^2$ is preferably a 5- or 6-membered ring. As specific preferred examples of the heterocycle $R^2$ there may be mentioned pyridine, pyrazine, pyrimidine, thiazole, oxazole, pyrazole and pyrrole.

As a substituent on the heterocycle, there may be mentioned halogen (which may be fluorine, chlorine, bromine or iodine), alkyl (among which a $C_1-C_4$ alkyl group is preferred, and methyl, ethyl or 1-methylethyl is particularly preferred), halogenated alkyl (a group wherein at least one of the hydrogen atoms of the alkyl group is substituted with a halogen atom: fluorine is preferred as the halogen atom and $C_1-C_4$ alkyl as the number of carbon atoms, with trifluoromethyl being particularly preferred), alkoxy (among which a $C_1-C_4$ alkoxy group is preferred, and methoxy is particularly preferred), a di($C_1-C_4$ alkyl)amino group and nitro. The number of substituents is not particularly limited, but is preferably 1 or 2. When two or more substituents are bonded to the heterocycle, they may be the same or different.

$R^3$ represents at least one moiety selected from the group consisting of hydrogen and $C_1-C_5$ alkyl, and it is preferably methyl. Methyl is also preferred in the definition of $R^4$ ($C_1-C_5$ alkyl group) given hereunder.

Preferred Combinations

The compounds of formula (I) comprising the preferred combinations of $R^1$, $R^2$, $R^3$ and n as described above are the preferred compounds in this invention; for example, the following compounds listed in Tables 1–9 may be mentioned as such.

TABLE 1

| compound no. | $R^2$<br>$R^3$<br>$(R^1)n$ |
|---|---|
| I-1 | 2-pyridyl<br>methyl<br>4-(1,1-dimethylethyl) |

TABLE 1-continued

| compound no. | R² / R³ / (R¹)n |
|---|---|
| I-2 | 4-pyridyl<br>methyl<br>4-(1,1-dimethylethyl) |
| I-3 | 6-chloro-3-pyridyl<br>hydrogen<br>4-(1,1-dimethylethyl) |
| I-4 | 6-chloro-3-pyridyl<br>methyl<br>4-(1,1-dimethylethyl) |
| I-5 | 6-bromo-3-pyridyl<br>methyl<br>4-(1,1-dimethylethyl) |
| I-6 | 6-fluoro-3-pyridyl<br>methyl<br>4-(1,1-dimethylethyl) |
| I-7 | 6-methyl-3-pyridyl<br>methyl<br>4-(1,1-dimethylethyl) |
| I-8 | 6-trifluoromethyl-3-pyridyl<br>methyl<br>4-(1,1-dimethylethyl) |
| I-9 | 6-methoxy-3-pyridyl<br>methyl<br>4-(1,1-dimethylethyl) |
| I-10 | 2-chloro-3-pyridyl<br>methyl<br>4-(1,1-dimethylethyl) |
| I-11 | 2,6-dichloro-3-pyridyl<br>methyl<br>4-(1,1-dimethylethyl) |

TABLE 2

| compound no. | R² / R³ / (R¹)n |
|---|---|
| I-12 | 5-chloro-2-pyrazyl<br>methyl<br>4-(1,1-dimethylethyl) |
| I-13 | 5-methyl-2-pyrazyl<br>methyl<br>4-(1,1-dimethylethyl) |
| I-14 | 5-chloro-6-methyl-2-pyrazyl<br>methyl<br>4-(1,1-dimethylethyl) |
| I-15 | 1-methyl-2-imidazolyl<br>methyl<br>4-(1,1-dimethylethyl) |
| I-16 | 6-chloro-3-pyridazyl<br>methyl<br>4-(1,1-dimethylethyl) |
| I-17 | 1-methyl-1H-pyrazol-4-yl<br>methyl<br>4-(1,1-dimethylethyl) |
| I-18 | 1,3-dimethyl-1H-pyrazol-4-yl<br>methyl<br>4-(1,1-dimethylethyl) |
| I-19 | 5-chloro-1-methyl-1H-pyrazol-4-yl<br>methyl<br>4-(1,1-dimethylethyl) |
| I-20 | 1,3,5-trimethyl-1H-pyrazol-4-yl<br>methyl<br>4-(1,1-dimethylethyl) |
| I-21 | 2-chloro-5-thiazolyl<br>methyl<br>4-(1,1-dimethylethyl) |
| I-22 | 5-isoxazolyl<br>methyl<br>4-(1,1-dimethylethyl) |

TABLE 3

| compound no. | R² / R³ / (R¹)n |
|---|---|
| I-23 | 6-chloro-3-pyridyl<br>methyl<br>2-chloro |
| I-24 | 6-chloro-3-pyridyl<br>methyl<br>4-chloro |
| I-25 | 6-chloro-3-pyridyl<br>methyl<br>2,4-dichloro |
| I-26 | 6-chloro-2-pyridyl<br>methyl<br>4-(1,1-dimethylethyl) |
| I-27 | 6-chloro-3-pyridyl<br>ethyl<br>4-(1,1-dimethylethyl) |
| I-28 | 6-chloro-3-pyridyl<br>1-methylethyl<br>4-(1,1-dimethylethyl) |
| I-29 | 4-chloro-2-pyridyl<br>methyl<br>4-(1,1-dimethylethyl) |
| I-30 | 1-ethyl-1H-pyrazol-4-yl<br>methyl<br>4-(1,1-dimethylethyl) |
| I-31 | 6-chloro-3-pyridyl<br>1,1-dimethylethyl<br>4-(1,1-dimethylethyl) |
| I-32 | 2-methyl-5-pyrimidyl<br>methyl<br>4-(1,1-dimethylethyl) |
| I-33 | 2,6-dichloro-5-pyrimidyl<br>methyl<br>4-(1,1-dimethylethyl) |

TABLE 4

| compound no. | R² / R³ / (R¹)n |
|---|---|
| I-34 | 2-methoxy-5-pyrimidyl<br>methyl<br>4-(1,1-dimethylethyl) |
| I-35 | 2-methylthio-5-pyrimidyl<br>methyl<br>4-(1,1-dimethylethyl) |
| I-36 | 2-pyrrolyl<br>methyl<br>4-(1,1-dimethylethyl) |
| I-37 | 1-methyl-2-pyrrolyl<br>methyl<br>4-(1,1-dimethylethyl) |
| I-38 | 6-chloro-3-pyridyl<br>methyl<br>3-chloro |
| I-39 | 6-chloro-3-pyridyl<br>methyl<br>2-methyl |
| I-40 | 6-chloro-3-pyridyl<br>methyl<br>2,6-dichloro |
| I-41 | 6-chloro-3-pyridyl<br>methyl<br>2-methoxy |
| I-42 | 6-chloro-3-pyridyl<br>methyl<br>2-trifluoromethyl |
| I-43 | 6-chloro-3-pyridyl<br>methyl<br>2,4-dimethyl |
| I-44 | 6-chloro-3-pyridyl<br>methyl<br>2-fluoro |

TABLE 5

| compound no. | R$^2$<br>R$^3$<br>(R$^1$)n |
|---|---|
| I-45 | 6-chloro-3-pyridyl<br>methyl<br>2-bromo |
| I-46 | 6-chloro-3-pyridyl<br>methyl<br>4-methyl |
| I-47 | 6-chloro-3-pyridyl<br>methyl<br>4-isopropyl |
| I-48 | 6-chloro-3-pyridyl<br>methyl<br>3-trifluoromethyl |
| I-49 | 6-chloro-3-pyridyl<br>methyl<br>3-trifluoromethoxy |
| I-50 | 6-chloro-3-pyridyl<br>methyl<br>3-iodo |
| I-51 | 6-chloro-3-pyridyl<br>methyl<br>3-isopropyloxy |
| I-52 | 6-chloro-3-pyridyl<br>methyl<br>3-nitro |
| I-53 | 6-chloro-3-pyridyl<br>methyl<br>3-hydroxy |
| I-54 | 6-chloro-3-pyridyl<br>methyl<br>3,4-dichloro |
| I-55 | 6-chloro-3-pyridyl<br>methyl<br>2,5-dichloro |

TABLE 6

| compound no. | R$^2$<br>R$^3$<br>(R$^1$)n |
|---|---|
| I-56 | 6-chloro-3-pyridyl<br>methyl<br>2,3-dichloro |
| I-57 | 6-chloro-3-pyridyl<br>methyl<br>3,5-dichloro |
| I-58 | 6-chloro-3-pyridyl<br>methyl<br>3,5-dimethoxy |
| I-59 | 6-chloro-3-pyridyl<br>methyl<br>3-chloro, 4-methoxy |
| I-60 | 6-chloro-3-pyridyl<br>methyl<br>3-chloro, 4-hydroxy |
| I-61 | 6-chloro-3-pyridyl<br>methyl<br>hydrogen |
| I-62 | 6-chloro-3-pyridyl<br>methyl<br>4-fluoro |
| I-63 | 6-chloro-3-pyridyl<br>methyl<br>4-trifluoromethyl |
| I-64 | 6-chloro-3-pyridyl<br>methyl<br>3,4-difluoro |
| I-65 | 6-chloro-3-pyridyl<br>methyl<br>3-bromo |

TABLE 6-continued

| compound no. | R$^2$<br>R$^3$<br>(R$^1$)n |
|---|---|
| I-66 | 6-chloro-3-pyridyl<br>methyl<br>3-methyl |

TABLE 7

| compound no. | R$^1$<br>R$^3$<br>(R$^1$)n |
|---|---|
| I-67 | 6-chloro-3-pyridyl<br>methyl<br>3-cyano |
| I-68 | 6-chloro-3-pyridyl<br>methyl<br>3-phenoxy |
| I-69 | 6-chloro-3-pyridyl<br>methyl<br>3-(1,1-dimethylethyl) |
| I-70 | 6-chloro-3-pyridyl<br>methyl<br>3-chloro, 4-fluoro |
| I-71 | 6-chloro-3-pyridyl<br>methyl<br>3-methyl, 4-nitro |
| I-72 | 6-chloro-3-pyridyl<br>methyl<br>3-methoxy, 4-chloro |
| I-73 | 6-chloro-3-pyridyl<br>methyl<br>3-hydroxy, 4-chloro |
| I-74 | 6-chloro-3-pyridyl<br>methyl<br>3,5-dimethyl |
| I-75 | 6-chloro-3-pyridyl<br>methyl<br>3-fluoro |
| I-76 | 6-chloro-3-pyridyl<br>methyl<br>3-methoxy |
| I-77 | 6-chloro-3-pyridyl<br>methyl<br>3-vinyl |

TABLE 8

| compound no. | R$^2$<br>R$^3$<br>(R$^1$)n |
|---|---|
| I-78 | 6-chloro-3-pyridyl<br>methyl<br>3-phenyl |
| I-79 | 6-chloro-3-pyridyl<br>methyl<br>4-phenyl |
| I-80 | 6-chloro-3-pyridyl<br>methyl<br>3,4-dimethyl |
| I-81 | 6-chloro-3-pyridyl<br>methyl<br>2-chloro, 5-trifluoromethyl |
| I-82 | 6-chloro-3-pyridyl<br>methyl<br>3-chloro, 4-methyl |
| I-83 | 6-chloro-3-pyridyl<br>methyl<br>3-bromo, 4-fluoro |
| I-84 | 6-chloro-3-pyridyl<br>methyl<br>3-trifluoromethyl, 4-fluoro |

TABLE 8-continued

| compound no. | R² R³ (R¹)n |
|---|---|
| I-85 | 6-chloro-3-pyridyl<br>methyl<br>3,4-dibromo |
| I-86 | 6-chloro-3-pyridyl<br>methyl<br>3-fluoro, 4-chloro |
| I-87 | 6-chloro-3-pyridyl<br>methyl<br>3-(2,2,2-trifluoroethoxy) |
| I-88 | 6-chloro-3-pyridyl<br>methyl<br>3-(1,1,2,2-tetrafluoroethoxy) |

TABLE 9

| compound no. | R² R³ (R¹)n |
|---|---|
| I-89 | 6-chloro-3-pyridyl<br>methyl<br>3-trifluoromethyl, 4-chloro |
| I-90 | 6-chloro-3-pyridyl<br>methyl<br>indan-5-yl *) |
| I-91 | 6-chloro-3-pyridyl<br>methyl<br>3,4-methylenedioxyphenyl *) |
| I-92 | 6-chloro-3-pyridyl<br>methyl<br>naphthalen-2-yl *) |

*): (R¹)n forms a ring together with the benzene ring.

Process for the Preparation of Propylamine Derivatives

Preferably, the N-heterocyclicmethylpropylamine derivatives of formula (I) as described above can be prepared by Route A or Route B as shown below.

[Reaction scheme (A), (B)]

Route A

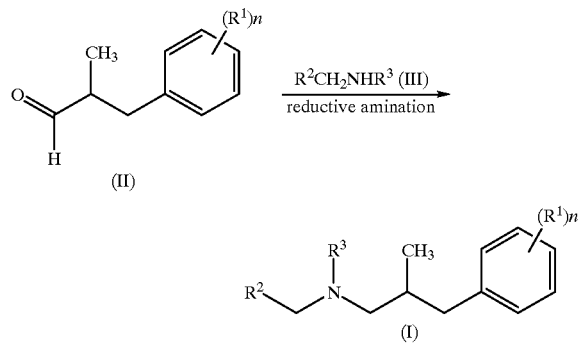

Route B

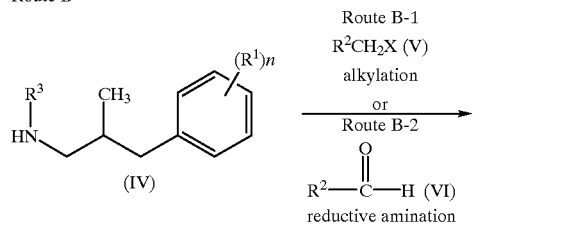

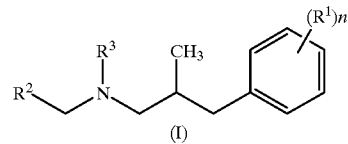

(in the above formulae $R^1$ represents a moiety selected from the group consisting of hydrogen, halogen, $C_1$–$C_6$ alkyl, $C_1$–$C_6$ alkenyl, $C_1$–$C_6$ halogenated alkyl, $C_1$–$C_6$ alkoxy, $C_1$–$C_6$ halogenated alkoxy, hydroxyl, cyano, nitro, phenyl optionally having a substituent on a ring thereof and phenoxy; n represents an integer of 0–5; when n is 2 or greater, each $R^1$ may be the same or different and two $R^1$ groups may be bonded together into a ring or crosslinked; $R^2$ represents a heterocycle containing at least one nitrogen atom as the hetero atom and optionally having a substituent on a ring thereof; $R^3$ represents at least one moiety selected from the group consisting of hydrogen and $C_1$–$C_5$ alkyl; and X represents a leaving group).

(Route A)

Employing reductive amination, a 3-phenylpropionaldehyde derivative of formula (II) is allowed to react with a heterocyclicmethylamine derivative of formula (III) in the presence of a reducing agent to synthesize an N-heterocyclicmethylpropylamine derivative of formula (I).

(Route B)

The nitrogen atom of the amino group of a 3-phenylpropylamine derivative of formula (IV) may be alkylated with a heterocycle-methylating agent of formula (V) to synthesize an N-heterocyclicmethylpropylamine derivative of formula (I) (Route B-1); or alternatively, reductive amination may be employed to synthesize an N-heterocyclicmethylpropylamine derivative of formula (I) by allowing a compound of formula (IV) to react with a heterocyclicaldehyde derivative of formula (VI) in the presence of a reducing agent (Route B-2).

[Reaction scheme (C)]

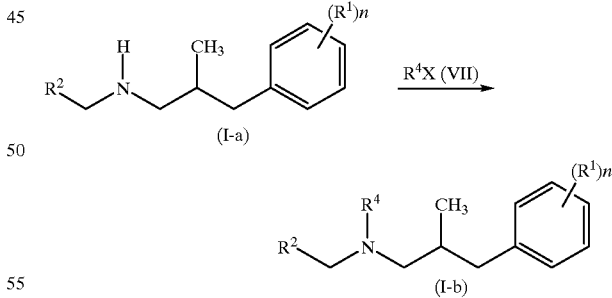

(in formulae (I-a), (I-b) and (VII) $R^1$, $R^3$, n and X are as previously defined, and $R^4$ represents $C_1$–$C_5$ alkyl).

As shown in reaction scheme (C) above, the nitrogen atom of the amino group of an N-heterocyclicmethylpropylamine derivative of formula (I-a) [a secondary amine equivalent to compound (I) wherein $R^3$=H] may be alkylated with a $C_1$–$C_5$ alkylating agent of formula (VII) to synthesize an N-alkyl-N-heterocyclicmethylpropylamine derivative of formula (I-b) [equivalent to compound (I) wherein $R^3$=$C_1$–$C_5$ alkyl].

(Starting Materials)

Several commercially available 3-phenylpropionaldehyde derivatives of formula (II) may be used as starting materials. Compounds (II) can be synthesized by the reaction shown below, referring to the method described in Tetrahedron Letters, 8, 597(1976).

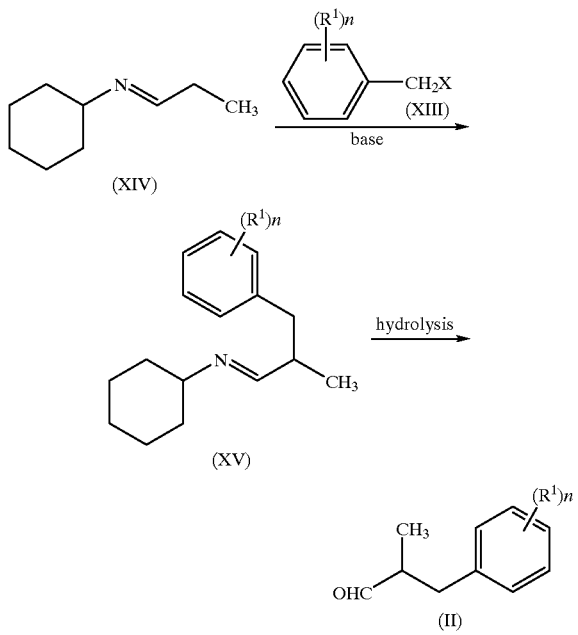

[Synthetic Schemes (1), (2)]

Synthetic Routes to 3-phenylpropylamine Derivatives

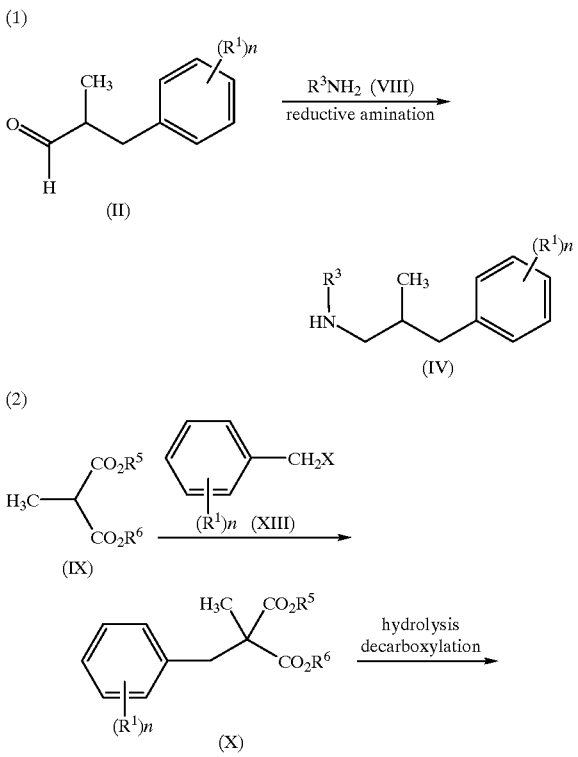

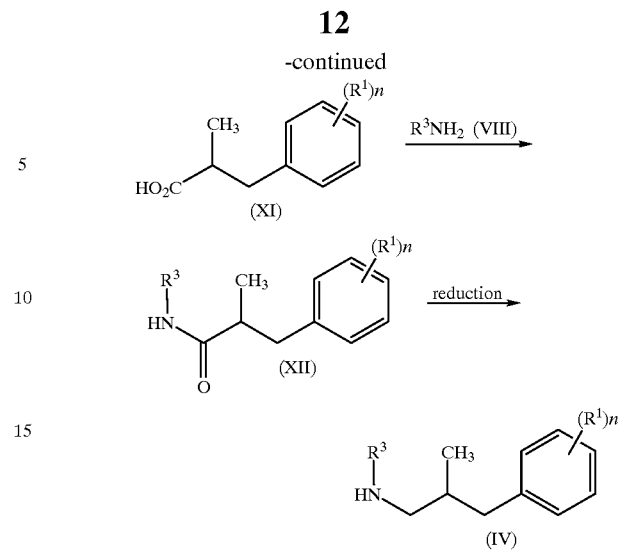

(in the above formulae $R^1$, $R^3$ and n are as previously defined, and $R^5$ and $R^6$ each independently represent $C_1$–$C_4$ alkyl).

A 3-phenylpropylamine derivative of formula (IV) may be obtained from a 3-phenylpropionaldehyde derivative of formula (II) and an aminating agent of formula (VIII) in the presence of a reducing agent, by using reductive amination such as that shown in synthetic schemes (1) and (2) above.

A 3-phenylpropylamine derivative of formula (IV) may also be prepared by using a methylmalonic acid diester (IX) (wherein $R^5$ and $R^6$ each independently represent $C_1$–$C_4$ alkyl) as the starting material, reacting it with a benzyl compound (XIII) in the presence of a base to produce a benzyl derivative (X); hydrolyzing and decarboxylating the benzyl derivative (X) to produce a carboxylic acid derivative (XI); converting the carboxylic acid derivative (XI) to a 3-phenylpropionamide derivative (XII) by the use of an aminating agent of formula (VIII); and then reducing compound (XII) with aluminum lithium hydride to obtain compound (IV).

The other starting compounds to be used in the invention include heterocyclicmethylamine derivatives of formula (III), aminating agents of formula (VIII), heterocycle-methylating agents of formula (V), $C_1$–$C_5$ alkylating agents of formula (VII), benzyl compounds of formula (XIII), heterocyclicaldehyde derivatives of formula (VI) and methylmalonic acid diesters of formula (IX).

Some of these compounds are described in the literature: see, for example, J. Heterocyclic. Chem., 5, 407 (1968); ibid., 6, 549 (1969); J. Org. Chem., 21, 97 (1956); Japanese Unexamined Patent Publication SHO No. 59-59669; Japanese Unexamined Patent Publication HEI No. 2-171; Aust. J. Chem., 21, 2251 (1974); and Chem. Pharm. Bull., 28 3057 (1980). Several of these compounds that are commercially available may also be used. They can also be synthesized utilizing the methods described in the literature, including those cited above.

(Amines)

The following compounds may be mentioned as a heterocyclicmethylamine derivative of formula (III): 2-pyridylmethylamine, 4-pyridylmethylamine, 6-chloro-3-pyridylmethylamine, 6-chloro-N-methyl-3-pyridylmethylamine, 6-fluoro-3-pyridylmethylamine, 6-fluoro-N-methyl-3-pyridylmethylamine, 5-chloro-2-pyrazylmethylamine, 5-chloro-N-methyl-2-pyrazylmethylamine, 2-chloro-3-pyridylmethylamine, 2-chloro-N-methyl-3-pyridylmethylamine, 2-chloro-5- thiazolylmethylamine, and 2-chloro-N-methyl-5-thiazolylmethylamine.

The following compounds may be mentioned as an aminating agent of formula (VIII): ammonia, methylamine, ethylamine, propylamine, isopropylamine, butylamine, isobutylamine, sec-butylamine, t-butylamine, pentylamine, and isopentylamine.

(Alkylating Agents)

The following compounds may be mentioned as a heterocycle-methylating agent of formula (V): 2-chloromethylpyridine, 4-chloromethylpyridine, 6-chloro-3-chloromethylpyridine, 6-bromo-3-bromomethylpyridine, 3-bromomethyl-6-fluoropyridine, 3-chloromethyl-6-methylpyridine, 3-bromomethyl-6-trifluoromethylpyridine, 3-bromomethyl-6-methoxypyridine, 2-chloro-3-chloromethylpyridine, 6-chloro-2-chloromethylpyridine, 4-chloro-2-chloromethylpyridine, 2,6-dichloro-3-chloromethylpyridine, 5-chloro-2-chloromethylpyrazine, 5-methyl-2-chloromethylpyrazine, 5-chloro-2-chloromethyl-6-methylpyrazine, 4-chloromethylpyrimidine, 2-chloro-5-chloromethylpyrimidine, 3-chloro-6-chloromethylpyridazine, 2-chloro-5-chloromethylthiazole, 5-bromomethylisoxazole, 5-chloro-4-chloromethyl-1-methylpyrazole, 6-chloro-2-chloromethylpyrazine, 4-chloro-2-chloromethylpyridine, and 2,6-dichloro-5-bromomethylpyrimidine.

The following compounds may be mentioned as a $C_1$–$C_5$ alkylating agent of formula (VII): methyl iodide, methyl bromide, ethyl bromide, ethyl iodide, isopropyl bromide, isopropyl iodide, butyl iodide, isobutyl iodide, sec-butyl iodide, pentyl iodide, isopentyl iodide, dimethyl sulfate, diethyl sulfate, and methyl p-toluenesulfonate.

The following compounds may be mentioned as a benzyl compound of formula (XIII): 2-chlorobenzyl chloride, 3-chlorobenzyl chloride, 4-chlorobenzyl chloride, 2-methylbenzyl chloride, 3-methylbenzyl chloride, 4-methylbenzyl chloride, 2-methoxybenzyl chloride, 3-methoxybenzyl chloride, 4-methoxybenzyl chloride, 2-trifluoromethylbenzyl chloride, 3-trifluoromethylbenzyl chloride, 4-trifluoromethylbenzyl chloride, 4-t-butylbenzyl bromide, 3,4-dichlorobenzyl chloride, 2,4-dichlorobenzyl chloride, 2,6-dichlorobenzyl bromide, 2,4-dimethylbenzyl chloride, 2,6-dimethylbenzyl chloride, 2-fluorobenzyl bromide, 2-bromobenzyl bromide, 3-trifluoromethoxybenzyl chloride, 3-iodobenzyl chloride, 3-isopropyloxybenzyl bromide, 3-nitrobenzyl bromide, 2,5-dichlorobenzyl chloride, 2,3-dichlorobenzyl chloride, 3,5-dichlorobenzyl chloride, 3,5-dimethoxybenzyl chloride, 3-chloro-4-methoxybenzyl bromide, 5-indanylmethyl chloride, 4-fluorobenzyl bromide, 3,4-difluorobenzyl bromide, 3-bromobenzyl bromide, 3-cyanobenzyl bromide, 3-phenoxybenzyl bromide, 3-t-butylbenzyl bromide, 3-chloro-4-fluorobenzyl bromide, 3-methyl-4-nitrobenzyl bromide, 3-methoxy-4-chlorobenzyl bromide, 3,5-dimethylbenzyl bromide, 3,4-methylenedioxybenzyl bromide, 3-fluorobenzyl bromide, 3-vinylbenzyl bromide, 3-phenylbenzyl bromide, 4-phenylbenzyl bromide, 3,4-dimethylbenzyl bromide, 2-chloro-5-trifluoromethylbenzyl bromide, 3-chloro-4-methylbenzyl bromide, 2-naphthylbenzyl chloride, 3-bromo-4-fluorobenzyl bromide, 3-trifluoromethyl-4-fluorobenzyl bromide, 3,4-dibromobenzyl bromide, 3-fluoro-4-chlorobenzyl bromide, 3-trifluoromethoxy-4-chlorobenzyl bromide, 3-chloro-4-fluoromethoxybenzyl bromide, and 3-trifluoromethyl-4-chlorobenzyl bromide.

(Aldehyde Compounds)

The following compounds may be mentioned as a heterocyclicaldehyde derivative of formula (VI): 6-chloro-3-pyridinecarboxaldehyde, 6-fluoro-3-pyridinecarboxaldehyde, 5-chloro-2-pyrazinecarboxaldehyde, 4-formyl-1-methylpyrazole, 4formyl-1,3-dimethylpyrazole, 4-formyl-1,3,5-trimethylpyrazole, 1-ethyl-4-formylpyrazole, 2-methyl-5-pyrimidinecarboxaldehyde, 2-methoxy-5-pyrimidinecarboxaldehyde, 2-methylthio-5-pyrimidinecarboxaldehyde, 2-pyrrolecarboxaldehyde, and 1-methyl-2-pyrrolecarboxaldehyde.

As the heterocycle-methylating agent of formula (V) containing a leaving group X, the $C_1$–$C_5$ alkylating agent of formula (VII) and the benzyl compound (XIII), which are materials for preparation of compounds (I) of the invention, there may be mentioned halides, sulfuric acid esters and (unsubstituted or substituted benzene) sulfonic acid esters.

As a suitable example of the leaving group X in these compounds, there may be mentioned halogen atoms such as chlorine, bromine and iodine, and p-toluenesulfonyloxy group.

(Reductive Amination)

The present specification will describe the steps of three different routes for reductive amination.

(1) Step of Route A in Reaction Scheme (A)

Synthesis of an N-heterocyclicmethylpropylamine derivative of formula (I) from a 3-phenylpropionaldehyde derivative of formula (II) and a heterocyclicmethylamine derivative of formula (III).

(2) Step of Route B-2 in Reaction Scheme (B)

Synthesis of an N-heterocyclicmethylpropylamine derivative of formula (I) from a 3-phenylpropylamine derivative of formula (IV) and a heterocyclicaldehyde derivative of formula (VI).

(3) Step of preparing an intermediate (IV) for Synthetic Scheme (1)

Among compounds (IV), the following compounds of formula (IV) have been described in the literature:

N,2-dimethyl-3-phenyl-propylamine,
N,2-dimethyl-3-(4-i-propylphenyl)-propylamine,
N-butyl-3-(4-t-butylphenyl)-2-methylpropylamine,
3-(4-t-butylphenyl)-N,2-dimethylpropylamine, and
3-(4-t-butylphenyl)-2-methyl-N-propylpropylamine.

Synthesis of a 3-phenylpropylamine derivative of formula (IV) from a 3-phenylpropionaldehyde derivative of formula (II) and an aminating agent of formula (VIII).

Such reductive amination may, for example, employ methods described in the literature: J. Am. Chem. Soc., 93, 2897 (1971); Synthesis, 135 (1975); Org. React., 4, 174 (1948); Tetrahedron Letters, 31, 5595 (1990); and J. Org. Chem., 61, 3849 (1996).

It is preferably carried out using a complex hydride compound (reducing agent), such as sodium cyanoborohydride or sodium triacetoxyborohydride, as the reducing agent. In addition to these, combinations of hydrogenation catalysts such as hydrogen gas and palladium/charcoal or Raney nickel, and formic acid, for example, can also be preferably used.

(Solvents for Reductive Amination)

The reductive amination can be carried out in a solvent or under solvent-free conditions. For the solvents that can be used then, those described below may be mentioned: alcohols such as methanol and ethanol; ethers such as tetrahydrofuran and dioxane; halogenated hydrocarbons such as 1,2-dichloroethane; water and acetonitrile. One kind of these solvents may be used alone; or, a mixed solvent containing at least one kind of these solvents may be used.

(Conditions for Reductive Amination)

The amount of the "reducing agent" (sodium cyanoborohydride, sodium triacetoxyborohydride or the like) to be used in the reductive amination described above is preferably 1.0–20.0 moles, and more preferably 1.0–3.0 moles, to each mole of the 3-phenylpropionaldehyde derivative of formula (II) or the heterocyclicaldehyde derivative of formula (VI). The amount of the heterocyclicmethylamine derivative of formula (III), the aminating agent of formula (VIII) or the 3-phenylpropylamine derivative of formula (IV) is preferably 0.5–3 moles, and more preferably 0.8–1.5 moles, to each mole of compound (II) or compound (VI).

Reaction temperatures for use are those in the range of from room temperature to the boiling points; but 20–50° C. is preferred.

(Alkylation)

Throughout the present specification, alkylation will be referred to for illustration of:

the step of synthesizing an N-heterocyclicmethylpropylamine derivative of formula (I) from a 3-phenylpropylamine derivative of formula (IV) and a heterocycle-methylating agent of formula (V), i.e. Route B-1 in Reaction Scheme (B) as described above;

the step of synthesizing an N-alkyl-N-heterocyclicmethylpropylamine derivative of formula (I-b) [equivalent to compound (I) wherein $R^3=C_1-C_5$] from an N-heterocyclicmethylpropylamine derivative of formula (I-a) (secondary amine) [equivalent to compound (I) wherein $R^3=H$] and a $C_1-C_5$ alkylating agent of formula (VII) in Reaction Scheme (C) as described above; and the step of synthesizing a benzyl derivative of formula (X) from a methylmalonic acid diester of formula (IX) and a benzyl compound of formula (XIII), and the step of synthesizing a benzylated imino compound of formula (XV) from an imino compound of formula (XIV) and a benzyl compound of formula (XIII) in Synthetic Scheme (2) as described above.

These steps may employ ordinary conditions for alkylation. The reaction can be carried out either in a solvent or under solvent-free conditions.

(Solvents for Alkylation)

The following may, for example, be mentioned as solvent: hydrocarbons such as benzene, toluene, xylene and hexane; halogenated hydrocarbons such as methylene chloride, chloroform and carbon tetrachloride; ethers such as diethyl ether, diisopropyl ether, tetrahydrofuran and dioxane; ketones such as acetone and methyl ethyl ketone; and others such as acetonitrile, dimethylformamide, 1-methyl-2-pyrrolidinone and dimethylsulfoxide.

(Bases)

From the standpoint of accelerating the alkylation described above, it is preferred that said reaction be carried out in the presence of a base. For bases that are used here, those described below may, for example be mentioned: inorganic bases such as sodium carbonate, potassium carbonate, sodium bicarbonate, sodium hydroxide and potassium hydroxide; the alkoxides of alkaline metals such as sodium methoxide, sodium ethoxide and potassium t-butoxide; alkaline metal hydrides such as sodium hydride and potassium hydride; the organometallic compounds of alkaline metals such as n-butyllithium; alkaline metal amides such as lithium diisopropylamide; and among others, organic tertiary amines such as triethylamine, pyridine, N,N-dimethylaniline and DBU (1,8-diazabicyclo[5.4.0] undec-7-ene). Among the bases described above, the inorganic bases such as potassium carbonate and sodium carbonate are usable most preferably.

The amount of the base to be used is preferably 1.0–10.0 moles, and more preferably 1.0–2.0 moles, to each mole of the 3-phenylpropylamine derivative of formula (IV) or the N-heterocyclicmethylpropylamine derivative of formula (I-a) (secondary amine) [equivalent to compound (I) wherein $R^3=H$].

(Alkylating Agents)

The amount of the heterocycle-methylating agent of formula (V), the $C_1-C_5$ alkylating agent of formula (VII) or the benzyl compound of formula (XIII) to be used is preferably 1.0–20 moles, and more preferably 1.0–4.0 moles, to each mole of compound (IV), compound (I-a) or compound (IX), respectively. Reaction temperatures for use during this alkylation are those in the range of from room temperature to the boiling points of the solvents; but 20–50° C. is preferred.

(Hydrolysis and Decarboxylation)

The hydrolysis and decarboxylation in the step of synthesizing the carboxylic acid derivative of formula (XI) from the benzyl derivative of formula (X) in Synthetic Scheme (2) may be carried out under either basic or acidic conditions.

When the reaction is carried out under basic conditions, it is preferred to use a lower alcohol or aromatic hydrocarbon in addition to water. The base used is preferably sodium hydroxide or potassium hydroxide. The reaction temperature is from 40° C. to the reflux point, and preferably from 70° C. to the reflux point.

When the reaction is carried out under acidic conditions, it is preferred to use acetic acid as a solvent in addition to water. The catalyst used may be an inorganic acid such as hydrochloric acid or hydrobromic acid. The reaction temperature is from 50° C. to the reflux point, and preferably from 80° C. to the reflux point.

(Amidation)

Amidation whereby a 3-phenylpropionamide derivative of formula (XII) is synthesized from a carboxylic acid derivative of formula (XI) and an aminating agent of formula (VIII) in Synthetic Scheme (2) described above may be carried out by allowing a carboxylic acid derivative of formula (XI) to react with an aminating agent of formula (VIII) in the presence of a condensation agent such as 1,3-dicyclohexylcarbodiimide (DCCD) or 1-ethyl-3-(3'-dimethylaminopropyl)carbodiimide (WSCI), or alternatively by converting a carboxylic acid derivative of formula (XI) to an acid chloride by reaction with thionyl chloride, phosphorus trichloride or oxalyl chloride, and then allowing to react it with an aminating agent of formula (VIII) in the presence of a base.

(Reduction)

The reduction reaction whereby a 3-phenylpropylamine derivative of formula (IV) is synthesized from a 3-phenylpropionamide derivative of formula (XII) in Synthetic Scheme (2) described above may be carried out by allowing an amide derivative of formula (XII) to react with a reducing agent such as lithium aluminum hydride or diborane. For example, the synthesis can be accomplished by the method described in Helv. Chim. Acta., (1948), 31, 1397 or J. Am. Chem. Soc., (1964), 86, 3566.

(Hydrolysis)

The hydrolysis of a benzylated imino compound of formula (XV) to a 3-phenylpropionaldehyde derivative of formula (II) is preferably carried out under acidic conditions.

The catalyst used may be an inorganic acid such as hydrochloric acid or hydrobromic acid, or an organic acid such as acetic acid or tartaric acid. The reaction temperature is ordinarily from −10 to 50° C., and preferably from 0 to 30° C.

The procedure is advantageously carried out by using the hydrolyzed reaction mixture directly for the reaction step of Route A, and for this procedure, the solvent is preferably tetrahydrofuran in combination with water.

(Purification Treatment)

The desired compounds (I) through the above-mentioned reactions can be obtained by carrying out ordinary purification treatment after completion of the reactions. More specifically, a reaction mixture as obtained from the reaction is poured into ice water. The organic layer is separated by extraction with an organic solvent such as ethyl acetate, chloroform, methylene chloride or benzene. Subsequently, this organic layer is washed with water and dried, and then, the solvent is removed under reduced pressure. The resulting residue is subjected to silica gel column chromatography or the like, which enables the purification treatment.

Optical isomers may exist for the N-heterocyclicmethylpropylamine derivative of formula (I) as obtained above, because there is an asymmetric carbon at the 2-position of its propyl group, regardless of any asymmetry due to other substituents. In this invention, compound (I) is intended to encompass any of the single isomers alone as well as mixtures of the respective optical isomers in any desired proportion.

(Acid Addition Salts)

Since compounds (I) can readily form acid addition salts, they may be used either in the form of inorganic acid salts or in the form of organic acid salts. For acids forming acid addition salts, there may be, for example, mentioned: inorganic acids such as hydrobromic acid, hydroiodic acid, nitric acid, sulfuric acid, and phosphoric acid; and organic acids such as formic acid, acetic acid, butyric acid, p-toluenesulfonic acid, maleic acid, succinic acid, fumaric acid, tartaric acid, citric acid, and salicylic acid.

(Preparation Intermediates)

For 3-phenylpropylamine derivatives of formula (IV), which are intermediates that can be used in the process for preparation of the compounds (I) of the invention as described above, there may be, for example, mentioned the compounds listed in Table 10 below.

TABLE 10

| compound no. | $R^3$ <br> $(R^1)n$ |
| --- | --- |
| IV-1 | methyl <br> 4-(1,1-dimethylethyl) |
| IV-2 | methyl <br> 2-chloro <br> 4-chloro |
| IV-3 | methyl |
| IV-4 | methyl <br> 2,4-dichloro |
| IV-5 | 1,1-dimethylethyl <br> 1,1-dimethylethyl |

Effective Ingredients for Agrochemicals

The compounds (I) of this invention can preferably be used as the effective ingredients for agrochemicals. Thus, when they are to be used as the effective ingredients for agrochemicals, the compounds (I) of the invention per se can be used as the agrochemical, but they are normally used, where necessary, after having been formulated together with formulating adjuvants to be used, into various forms such as dusting powders, wettable powders, granules, and emulsifiable concentrates.

In such cases, it is preferred that the preparation be formulated so as to contain one or more compounds of the invention in an amount of 0.1–95 wt % (in total), more favorably 0.5–90 wt %, and particularly 2–70 wt %, in the agrochemical preparation based on its total amount (100 wt %) which contains the compound(s) of the invention per se.

Suitable carriers, diluents and surfactants which are usable as formulating adjuvants are mentioned in the following:

Solid carriers: talc, kaolin, bentonite, diatomaceous earth, white carbon, clay, etc.

Liquid diluents: water, xylene, toluene, chlorobenzene, cyclohexane, cyclohexanone, dimethylsulfoxide, dimethylformamide, alcohol, etc.

Surfactants: preferably, they may be used, where appropriate, depending on their effects. As emulsifying agents: polyoxyethylenealkyl allyl ethers, polyoxyethylene sorbitan monolaurate, etc. As dispersing agents: lignin sulfonate, dibutyl naphthalenesulfonate, etc. As wetting agenst: alkylsulfonates, alkylphenylsulfonates, etc.

(Dilution)

Some of the aforementioned agrochemical preparations are in the form for use as such, and others are in the form for use after having been diluted to their predetermined concentrations with diluents such as water. Where the use after dilution is intended, the concentration of a compound of the invention after the dilution is preferably in the range of 0.001–1.0%. The use level of the compound of the invention is preferably in the range of 20–5000 g, and more preferably 50–1000 g, per hectare (ha) of the farming or horticultural land, such as a field, rice paddy, orchard or greenhouse.

Because these concentrations and levels for use will vary according to the form of preparation, the period, method and location of application, the crop objects and other factors, they can be above or below the above-mentioned ranges where necessary.

Further, the compounds of this invention may, if necessary, be used in combination with other effective ingredients such as microbicides, insecticides, miticides, herbicides and the like.

This invention will now be explained in greater detail by referring to preparation examples, reference preparation examples, formulation examples and test examples; however, the invention is not to be limited to the following preparation examples, formulation examples or test examples insofar as it does not depart from the gist thereof.

EXAMPLES

Preparation Example 1

N-[3-(4-t-Butylphenyl)-2-methylpropyl]-6-chloro-3-pyridylmethylamine (I-3) (Indicating the Compound Number in the Tables and so Forth Hereunder)

Route A: After suspending 620 mg (9.84 mmol) of sodium cyanoborohydride in 2 ml of absolute methanol, 700 mg (4.91 mmol) of 6-chloro-3-pyridylmethylamine was added thereto. Subsequently, to this was added a solution of 1.0 g (4.90 mmol) 3-(4-t-butylphenyl)-2-methylpropionaldehyde/2 ml absolute methanol by portions and then, stirring was conducted at room temperature for 4 h.

Methanol was removed under reduced pressure, water was added and extraction with methylene chloride was done. The resulting methylene chloride layer was washed with saturated brine and dried over anhydrous sodium sulfate. The solvent was removed under reduced pressure and the residue was purified with a silica gel (Silica gel 60, 230–400 mesh, Merck Co.) column [eluent composition: n-Hex (n-hexane)/AcOEt (ethyl acetate)=1/1] to afford 510 mg of the desired compound (I-3) as an oil. The yield was 31.5%.

Preparation Example 2

N-[3-(4-t-Butylphenyl)-2-methylpropyl]-6-chloro-N-methyl-3-pyridylmethylamine (I-4)

Method for alkylation of compound (I-a): After dissolving 170 mg (0.51 mmol) of N-[3-(4-t-butylphenyl)-2- methylpropyl]-6-chloro-3-pyridylmethylamine (I-3) in 1 ml of DMF (N,N-dimethylformamide), 163 mg (1.15 mmol) of methyl iodide was added thereto. Subsequently, to this was added 70 mg of sodium carbonate and stirring was conducted at room temperature for 7 h and at 50° C. for 1 h.

After standing to cool, the resulting reaction solution was poured into water and extraction with benzene was done. The benzene layer was washed with saturated brine and dried over anhydrous sodium sulfate. The solvent was removed under reduced pressure and the residue was purified with a silica gel (Silica gel 60, 230–400 mesh, Merck Co.) column [eluent composition: n-Hex/AcOEt=10/1] to afford 160 mg of the desired compound (I-4) as a colorless oil. The yield was 91.1%.

Preparation Example 3

6-Chloro-N-[(3-chloro-4-fluorophenyl)-2-methylpropyl]-3-pyridylmethylamine (I-70)

Route A: After dissolving 260 mg (1.30 mmol) of (3-chloro-4-fluorophenyl)-2-methylpropionaldehyde and 230 mg (1.47 mmol) of 6-chloro-N-methyl-3-pyridylmethylamine in 4 ml of anhydrous 1,2-dichloroethane, 320 mg (1.51 mmol) of sodium triacetoxyborohydride was added thereto while stirring, and stirring was continued at room temperature for 1 h.

Saturated sodium bicarbonate solution was added to the reaction solution to pH 8, and extraction with methylene chloride was done. The methylene chloride layer was dried over anhydrous sodium sulfate. The solvent was removed under reduced pressure and the residue was purified with a silica gel (Silica gel 60, 230–400 mesh, Merck Co.) column [eluent composition: n-Hex/AcOEt=5/1] to afford 380 mg of the desired compound (I-70) as an oil. The yield was 85.7%.

Preparation Example 4

N-[3-(4-t-Butylphenyl)-2-methylpropyl]-6-chloro-N-methyl-3-pyridylmethylamine (I-4)

Route B-1: After suspending 6.2 g (98.4 mmol) of sodium cyanoborohydride in 20 ml of absolute methanol, 6.6 g (97.8 mmol) of methylamine hydrochloride was added thereto. Subsequently, to this was added a solution of 10.0 g (49.0 mmol) 3-(4-t-butylphenyl) propionaldehyde/15 ml absolute methanol by portions and then, stirring was conducted at room temperature for 9 h.

Methanol was removed under reduced pressure, water was added, the pH was adjusted to 11 with a 2 N sodium hydroxide solution, and extraction with methylene chloride was done. The methylene chloride layer was washed with saturated brine and dried over anhydrous sodium sulfate. The solvent was removed to afford 11.2 g of an oil. This was purified with a silica gel (Wakogel C-200) column [AcOEt (for elution of impurities) and methanol (for elution of desired product)] to afford 4.15 g of 3-(4-t-butylphenyl)-N,2-dimethylpropylamine (IV-1). The yield was 38.7%.

After dissolving 500 mg (2.3 mmol) of the obtained compound (IV-1) above in 2 ml of DMF, 330 mg (2.0 mmol) of 6-chloro-3-chloromethylpyridine was added. Subsequently, to this was added 320 mg of potassium carbonate and then, stirring was conducted at room temperature for 8 h.

The reaction solution was poured into water and extraction with benzene was done. The benzene layer was washed with saturated brine and dried over anhydrous sodium sulfate. The solvent was removed under reduced pressure to afford 890 mg of an oil. This was purified with a silica gel (Silica gel 60, 230–400 mesh, Merck Co.) column [eluent composition: n-Hex/AcOEt=10/1] to afford 700 mg of the desired compound (I-4) as a colorless oil. The yield was 89.1%.

Preparation Example 5

N-[3-(4-t-Butylphenyl)-2-methylpropyl]-5-chloro-N-methyl-2-pyrazylmethylamine (I-12)

Route B-1: After dissolving 220 mg (1.0 mmol) of 3-(4-t-butylphenyl)-N,2-dimethylpropylamine (IV-1) in 1.5 ml of DMF, 145 mg (0.89 mmol) of 5-chloro-2-chloromethylpyrazine was added thereto. Subsequently, to this was added 140 mg of potassium carbonate and stirring was conducted at room temperature for 8 h.

The reaction solution was poured into water and extraction with benzene was done. The benzene layer was washed with saturated brine and dried over anhydrous sodium sulfate. The solvent was removed under reduced pressure to afford 310 mg of an oil. This was purified with a silica gel (Silica gel 60, 230–400 mesh, Merck Co.) column (eluent composition: n-Hex/AcOEt=15/1) to afford 240 mg of the desired compound (I-12) as a colorless oil. The yield was 78.1%.

Preparation Example 6

N-[3-(4-t-Butylphenyl)-2-methylpropyl]-N,1-dimethyl-1H-pyrazol-4-ylmethylamine (I-17)

Route B-2: After suspending 200 mg (3.2 mmol) of sodium cyanoborohydride in 2 ml of absolute methanol, 380 mg (1.7 mmol) of 3-(4-t-butylphenyl)-N,2-dimethylpropylamine (IV-1) was added thereto. Subsequently, to this was added a solution of 170 mg (1.6 mmol) 4-formyl-1-methylpyrazole/2 ml absolute methanol by portions, the pH was adjusted to 7 with acetic acid, and then stirring was conducted at room temperature for 8 h.

Methanol was removed under reduced pressure, water was added and extraction with ethyl acetate was done. The ethyl acetate layer was washed with saturated brine and dried over anhydrous sodium sulfate. The solvent was removed under reduced pressure and the residue was purified with a silica gel (Silica gel 60, 230–400 mesh, Merck Co.) column (eluent composition: n-Hex/AcOEt=1/1) to afford 340 mg of the desired compound (I-17) as an oil. The yield was 70.1%.

The following Tables 11–21 list the types of preparation method (Route B-1 or Route B-2) for compounds that were prepared by manipulations following Preparation Examples 1–6 with or without modifications (when alkylation was carried out after Route A, this is also indicated), and their NMR data. These tables also include compound (I-3), compound (I-4), compound (I-12), compound (I-17) and compound (I-70).

TABLE 11

| compound no. | $^1$H-NMR (δ, ppm) |
|---|---|
| type of preparation method: | |
| Route A | |
| Route B-1 | |
| Route B-2 | |

TABLE 11-continued

| compound no. | $^1$H-NMR ($\delta$, ppm) |
|---|---|
| I-1<br>Route B-1 | 0.85(d, 3H, J = 6 Hz), 1.27(s, 9H),<br>1.58–3.08(m, 5H), 2.22(s, 3H), 3.58(s, 2H),<br>6.97(d, 2H, J = 8 Hz), 6.97(d, 2H, J = 8 Hz),<br>7.22(d, 2H, J = 8 Hz), 6.85–7.62(m, 3H),<br>8.32–8.53(m, 1H) |
| I-2<br>Route B-1 | 0.85(d, 3H, J = 6 Hz), 1.27(s, 9H),<br>1.70–3.00(m, 5H), 2.13(s, 3H), 3.42(s, 2H),<br>7.02(d, 2H, J = 8 Hz), 7.22(d, 2H, J = 6 Hz),<br>7.25(d, 2H, J = 8 Hz), 8.48(d, 2H, J = 6 Hz) |
| I-3<br>Route A | 0.87(d, 3H, J = 6Hz), 1.25(s, 9H),<br>1.53–2.83(m, 6H), 3.63(s, 2H),<br>6.93(d, 2H, J = 8 Hz), 7.13(d, 1H, J = 8 Hz),<br>7.20(d, 2H, J = 8 Hz), 7.52(dd, 1H, J = 2, 8 Hz),<br>8.20(d, 1H, J = 2 Hz) |
| I-4<br>Route B-1 | 0.82(d, 3H, J = 6 Hz), 1.27(s, 9H),<br>1.53–3.00(m, 5H), 2.13(s, 3H), 3.40(s, 2H),<br>6.90(d, 2H, J = 8 Hz), 7.18(d, 1H, J = 8 Hz),<br>7.22(d, 2H, J = 8 Hz), 7.57(dd, 1H, J = 2, 8 Hz),<br>8.22(d, 1H, J = 2 Hz) |
| I-5<br>Route B-1 | 0.82(d, 3H, J = 6 Hz), 1.27(s, 9H),<br>1.67–2.93(m, 5H), 2.13(s, 3H), 3.37(s, 2H),<br>6.97(d, 2H, J = 8 Hz), 7.23(d, 2H, J = 8 Hz),<br>7.23–7.50(m, 2H), 8.23(d, 1H, J = 2 Hz) |
| I-6<br>Route B-1 | 0.83(d, 3H, J = 6 Hz), 1.27(s, 9H),<br>1.87–3.07(m, 5H), 2.13(s, 3H), 3.40(s, 2H),<br>6.77(dd, 1H, J = 3, 8 Hz), 6.95(d, 2H, J = 8 Hz),<br>7.20(d, 2H, J = 8 Hz),<br>7.68(ddd, 1H, J = 3, 8, 8 Hz),<br>8.02(d, 1H, J = 3 Hz) |
| I-7<br>Route B-1 | 0.83(d, 3H, J = 6 Hz), 1.27(s, 9H),<br>1.80–3.17(m, 5H), 2.12(s, 3H), 2.48(s, 3H),<br>3.37(s, 2H), 6.95(d, 2H, J = 8 Hz),<br>7.20(d, 2H, J = 8 Hz), 6.87–7.60(m, 2H),<br>8.33(d, 1H, J = 2 Hz) |

TABLE 12

| compound no. | $^1$H-NMR ($\delta$, ppm) |
|---|---|
| type of preparation method:<br>Route A<br>Route B-1<br>Route B-2 | |
| I-8<br>Route B-1 | 0.87(d, 3H, J = 6Hz), 1.28(s, 9H),<br>1.73–3.00(m, 5H), 2.17(s, 3H), 3.52(s, 2H),<br>6.98(d, 2H, J = 8 Hz), 7.25(d, 2H, J = 8 Hz),<br>7.55(d, 1H, J = 8 Hz), 7.80(dd, 1H, J = 2, 8 Hz),<br>8.60(d, 1H, J = 2 Hz) |
| I-9<br>Route B-1 | 0.85(d, 3H, J = 6 Hz), 1.30(s, 9H),<br>1.97–3.00(m, 5H), 2.15(s, 3H), 3.37(s, 2H),<br>3.90(s, 3H), 6.65(d, 1H, J = 8 Hz),<br>7.00(d, 2H, J = 8 Hz), 7.25(d, 2H, J = 8 Hz),<br>7.5(dd, 1H, J = 2, 8 Hz), 7.97(d, 1H, J = 2 Hz) |
| I-10<br>Route B-1 | 0.85(d, 3H, J = 6 Hz), 1.27(s, 9H),<br>1.57–3.00(m, 5H), 2.20(s, 3H), 3.53(s, 2H),<br>6.98(d, 2H, J = 8 Hz),<br>7.23(d, 2H, J = 8 Hz), 6.97–7.30(m, 1H),<br>7.83(dd, 1H, J = 2, 8 Hz),<br>8.22(d, 1H, J = 2, 5Hz) |
| I-11<br>Route B-1 | 0.85(d, 3H, J = 6 Hz), 1.27(s, 9H),<br>1.50–3.00(m, 5H),<br>2.17(s, 3H), 3.48(s, 2H), 6.98(d, 2H, J = 8 Hz),<br>7.18(d, 1H, J = 8 Hz), 7.25(d, 2H, J = 8Hz),<br>7.82(d, 1H, J = 8 Hz) |
| I-12<br>Route B-1 | 0.82(d, 3H, J = 6 Hz), 1.25(s, 9H),<br>1.65–2.92(m, 5H), 2.20(s, 3H), 3.58(s, 2H),<br>6.95(d, 2H, J = 8 Hz), 7.20(d, 2H, J = 8 Hz),<br>8.40(s, 2H) |
| I-13<br>Route B-1 | 0.85(d, 3H, J = 6 Hz), 1.27(s, 9H),<br>1.70–2.93(m, 5H), 2.23(s, 3H), 2.50(s, 3H),<br>3.60(s, 2H), 7.00(d, 2H, J = 8 Hz),<br>7.23(d, 2H, J = 8 Hz), 8.32(d, 1H, J = 1 Hz),<br>8.55(d, 1H, J = 1 Hz) |

TABLE 12-continued

| compound no. | $^1$H-NMR ($\delta$, ppm) |
|---|---|
| I-14<br>Route B-1 | 0.92(d, 3H, J = 6 Hz), 1.35(s, 9H),<br>1.77–2.93(m, 5H), 2.3(s, 3H), 2.67 (s, 3H),<br>3.65(s, 2H), 7.03(d, 2H, J = 8 Hz),<br>7.28(d, 2H, J = 8 Hz), 8.33(s, 1H) |
| I-15<br>Route B-2 | 0.78(d, 3H, J = 6 Hz), 1.30(s, 9H),<br>1.57–2.93(m, 5H), 2.12(s, 3H),<br>3.48(s, 2H), 3.62(s, 3H), 6.68(d, 1H, J = 1 Hz),<br>6.78(d, 1H, J = 1 Hz), 6.90(d, 2H, J = 8 Hz),<br>7.17(d, 2H, J = 8 Hz) |

TABLE 13

| compound no. | $^1$H-NMR ($\delta$, ppm) |
|---|---|
| type of preparation method:<br>Route A<br>Route B-1<br>Route B-2 | |
| I-16<br>Route B-1 | 0.83(d, 3H, J = 6 Hz), 1.28(s, 9H),<br>1.43–2.97(m,5H), 2.20(s, 3H), 3.77(s, 2H),<br>6.98(d, 2H, J = 8 Hz), 7.23(d, 2H, J = 8 Hz),<br>7.37(d, 1H, J = 9 Hz), 7.63(d, 1H, J = 9 Hz) |
| I-17<br>Route B-2 | 0.83(d, 3H, J = 6 Hz,), 1.28(d, 9H),<br>1.98–2.98(m, 5H), 2.13(s, 3H), 3.33(s, 2H),<br>3.78(s, 3H), 6.97(d, 2H, J = 8 Hz), 7.13(s, 1H)<br>7.18(d, 2H, J = 8 Hz), 7.28(s, 1H) |
| I-18<br>Route B-2 | 0.80(d, 3H, J = 6 Hz), 1.27(s, 9H),<br>1.80–2.93(m, 5H), 2.10(s, 3H), 2.20(s, 3H),<br>3.23(s, 2H), 3.72(s, 3H), 6.97(d, 2H, J = 8 Hz),<br>7.05(s, 1H), 7.23(d, 2H, J = 8 Hz) |
| I-19<br>Route B-2 | 0.83(d, 3H, J = 6 Hz), 1.28(s, 9H),<br>1.63–2.93(m, 5H), 2.13(s, 3H), 3.33(s, 2H),<br>3.75(s, 3H), 6.98(d, 2H, J = 8 Hz),<br>7.22(d, 2H, J = 8 Hz), 7.32(s, 1H) |
| I-20<br>Route B-2 | 0.78(d, 3H, J = 6 Hz), 1.28(s, 9H),<br>1.73–2.97(m, 5H), 2.05(s, 3H), 2.15(s, 6H),<br>3.13(s, 2H), 3.62(s, 3H), 6.93(d, 2H, J = 8 Hz),<br>7.18(d, 2H, J = 8 Hz) |
| I-21<br>Route B-1 | 0.85(d, 3H, J = 6 Hz), 1.28(s, 9H),<br>1.67–2.93(m, 5H), 2.20(s, 3H), 3.58(s, 2H),<br>7.00(d, 2H, J = 8 Hz), 7.25(d, 2H, J = 8 Hz),<br>7.25(s, 1H) |
| I-22<br>Route B-1 | 0.85(d, 3H, J = 6 Hz), 1.28(s, 9H),<br>1.62–2.95(m, 5H), 2.25(s, 3H), 3.67(s, 2H),<br>6.02(d, 1H, J = 2 Hz), 7.00(d, 2H, J = 8 Hz),<br>7.25(d, 2H, J = 8 Hz), 8.08(d, 1H, J = 2 Hz) |
| I-23<br>Route B-1 | 0.78(d, 3H, J = 6 Hz), 1.67–3.27(m, 5H),<br>2.10(s, 3H), 3.35(s, 2H), 6.93–7.33(m, 4H),<br>7.15(d, 1H, J = 8 Hz), 7.55(dd, 1H, J = 2, 8 Hz),<br>8.18(d, 1H, J = 2 Hz) |
| I-24<br>Route B-1 | 0.82(d, 3H, J = 6 Hz), 1.63–3.08(m, 5H),<br>2.15(s, 3H), 3.42(s, 2H), 6.98(d, 2H, J = 8 Hz),<br>7.210(d, 2H, J = 8 Hz), 7.22(d, 1H, J = 8 Hz),<br>7.58(dd, 8.25(d, 1H, J = 2 Hz) |
| I-25<br>Route B-1 | 0.82(d, 3H, J = 6 Hz), 1.67–3.27(m, 5H),<br>2.15(d, 3H), 3.42(s, 2H), 6.93–7.37(m, 3H),<br>7.20(d, 1H, J = 8 Hz), 7.58(dd, 1H, J = 2, 8 Hz),<br>8.25(d, 1H, J = 2 Hz) |

TABLE 14

| compound no. | $^1$H-NMR ($\delta$, ppm) |
|---|---|
| type of preparation method:<br>Route A<br>Route B-1<br>Route B-2 | |
| I-26 | 0.85(d, 3H, J = 6Hz), 1.28(s, 9H), |

TABLE 14-continued

| compound no. | $^1$H-NMR (δ, ppm) |
|---|---|
| Route B-1 | 1.57–3.07(m, 5H), 2.23(s, 3H), 3.58(s, 2H), 7.00(d, 2H, J = 8 Hz), 7.25(d, 2H, J = 8 Hz), 6.90–7.73(m, 3H), |
| I-27 Route A and alkylation | 0.80(d, 3H, J = 6 Hz), 0.97(t, 3H, J = 7 Hz), 1.27(s, 9H), 1.48–2.92(m, 5H), 2.43(q, 2H, J = 7Hz), 3.43(s, 2H), 6.92(d, 2H, J = 8 Hz), 7.12(d, 1H, J = 8 Hz), 7.18(d, 2H, J = 8 Hz), 7.53(dd, 1H, J = 2, 8 Hz), 8.20(d, 1H, J = 2 Hz) |
| I-28 Route A and alkylation | 0.78(d, 3H, J = 6 Hz), 0.98(d, 6H, J = 6 Hz), 1.28(s, 9H), 1.53–3.20(m, 6H), 3.50(s, 2H), 6.97(d, 2H, J = 8 Hz), 7.23(d, 1H, J = 8 Hz), 7.27(d, 2H, J = 8 Hz), 7.68(dd, 1H, J = 2, 8 Hz), 8.33(d, 1H, J = 2 Hz) |
| I-29 Route B-1 | 0.85(d, 3H, J = 6 Hz), 1.27(s, 9H), 1.58–3.05(m, 5H), 2.20(s, 3H), 3.57(s, 2H), 6.97(d, 2H, J = 8 Hz), 6.95–7.22(m, 1H), 7.22(d, 2H, J = 8 Hz), 7.47(d, 1H, J = 2 Hz), 8.33(d, 1H, J = 5 Hz) |
| I-30 Route B-2 | 0.82(d, 3H, J = 6 Hz), 1.28(s, 9H), 1.42(t, 3H, J = 7Hz), 1.90–3.10(m, 5H), 2.13(s, 3H), 3.35(s, 2H), 4.05(q, 2H, J = 7 Hz), 6.98(d, 2H, J = 8 Hz), 7.17(s, 1H), 7.23(d, 2H, J = 8 Hz), 7.30(s, 1H) |
| I-31 Route B-1 | 0.73(d, 3H, J = 6 Hz), 1.02(s, 9H), 1.23(s, 9H), 1.37–1.77(m, 1H), 1.97(dd, 1H, J = 8, 13 Hz), 2.37(d, 2H, J = 6 Hz), 2.73(dd, 1H, J = 4, 13 Hz), 3.55(s, 2H), 6.75(d, 2H, J = 8 Hz), 7.10(d, 1H, J = 8 Hz), 7.13(d, 2H, J = 8 Hz), 7.60(dd, 1H, J = 2, 8 Hz), 8.25(d, 1H, J = 2 Hz) |
| I-32 Route B-1 | 0.85(d, 3H, J = 6 Hz), 1.28(s, 9H), 1.67–2.93(m, 5H), 2.17(s, 3H), 2.70(s, 3H), 3.40(s, 2H), 7.00(d, 2H, J = 8 Hz), 7.27(d, 2H, J = 8 Hz), 8.55(s, 2H) |
| I-33 Route B-1 | 0.85(d, 3H, J = 6 Hz), 1.27(s, 9H), 1.87–3.10(m, 5H), 2.18 (s, 3H), 3.48(s, 2H), 6.93(d, 2H, J = 8 Hz), 7.20(d, 2H, J = 8 Hz), 8.57(s, 1H) |
| I-34 Route B-2 | 0.83(d, 3H, J = 6 Hz), 1.27(s, 9H), 1.58–2.92(m, 5H), 2.12(s, 3H), 3.33(s, 2H), 3.92(s, 3H), 6.95(d, 2H, J = 8 Hz), 7.20(d, 2H, J = 8 Hz), 8.35(s, 2H) |

TABLE 15

| compound no. | $^1$H-NMR (δ, ppm) |
|---|---|
| type of preparation method: Route A Route B-1 Route B-2 | |
| I-35 Route B-2 | 0.85(d, 3H, J = 6 Hz), 1.27(s, 9H), 1.67–3.00(m, 5H), 2.13(s, 3H), 2.53(s, 3H), 3.37(s, 2H), 6.98(d, 2H, J = 8 Hz), 7.23(d, 2H, J = 8 Hz), 8.40(s, 2H) |
| I-36 Route B-2 | 0.83(d, 3H, J = 6 Hz), 1.28(s, 9H), 1.62–2.95(m, 5H), 2.12(s, 3H), 3.42(s, 2H), 5.82–6.15(m, 2H), 6.55–6.75(m, 1H), 7.00(d, 2H, J = 8 Hz), 7.25(d, 2H, J = 8 Hz) |
| I-37 Route B-2 | 0.77(d, 3H, J = 6 Hz), 1.28(s, 9H), 1.72–2.95(m, 5H), 2.08(s, 3H), 3.32(s, 2H), 3.58(s, 3H), 5.92(d, 2H, J = 3 Hz), 6.50(dd, 1H, J = 3Hz), 6.95(d, 2H, J = 8 Hz), 7.20(d, 2H, J = 8 Hz) |
| I-38 Route A | 0.82(d, 3H, J = 6 Hz), 1.60–3.00(m, 5H), 2.13(s, 3H), 3.40(s, 2H), 6.77–7.33(m, 5H), 7.58(dd, 1H, J = 2, 8 Hz), 8.25(d, 1H, J = 2 Hz) |
| I-39 Route A | 0.87(d, 3H, J = 6 Hz), 1.57–3.07(m, 5H), 2.17(s, 3H), 2.27(s, 3H), 3.42(s, 2H), 6.93–7.23(m, 4H), 7.20(d, 1H, J = 8 Hz), 7.60(dd, 1H, J = 2, 8 Hz), 8.27(d, 1H, J = 2 Hz) |
| I-40 | 0.87(d, 3H, J = 6 Hz), 1.83–3.30(m, 5H), |

TABLE 15-continued

| compound no. | $^1$H-NMR (δ, ppm) |
|---|---|
| Route A | 2.13(s, 3H), 3.42(s, 2H), 6.83–7.40(m, 4H), 7.60(dd, 1H, J = 2, 8 Hz), 8.25(d, 1H, J = 2 Hz) |
| I-41 Route A | 0.80(d, 3H, J = 6 Hz), 1.70–3.23(m, 5H), 2.13(s, 3H), 3.40(s, 2H), 3.70(s, 3H), 6.60–7.33(m, 5H), 7.60(dd, 1H, J = 2, 8 Hz), 8.23(d, 1H, J = 2 Hz) |
| I-42 Route A | 0.83(d, 3H, J = 6 Hz), 1.78–3.28(m, 5H), 2.13(s, 3H), 3.40(s, 2H), 6.98–1.70(m, 5H), 7.58(dd, 1H, J = 2, 8 Hz), 8.22(d, 1H, J = 2 Hz) |
| I-43 Route A | 0.83(d, 3H, J = 6 Hz), 1.75–3.22(m, 5H), 2.13(s, 3H), 2.22(s, 3H), 2.25(s, 3H), 3.40(s, 2H), 6.78–7.08(m, 3H), 7.18(d, 1H, J = 8 Hz), 7.60(dd, 1H, J = 2, 8 Hz), 8.23(d, 1H, J = 2 Hz) |

TABLE 16

| compound no. | $^1$H-NMR (δ, ppm) |
|---|---|
| type of preparation method: Route A Route B-1 Route B-2 | |
| I-44 Route A | 0.83(d, 3H, J = 6 Hz), 1.67–3.17(m, 5H), 2.13(s, 3H), 3.42(s, 2H), 6.67–7.25(m, 4H), 7.20(d, 1H, J = 8 Hz), 7.60(dd, 1H, J = 2, 8 Hz), 8.25(d, 1H, J = 2 Hz) |
| I-45 Route A | 0.83(d, 3H, J = 6 Hz), 1.63–3.20(m, 5H), 2.17(s, 3H), 3.43(s, 2H), 6.93–7.47(m, 5H), 7.60(dd, 1H, J = 2, 8 Hz), 8.23(d, 1H, J = 2 Hz) |
| I-46 Route A | 0.82(d, 3H, J = 6 Hz), 1.77–3.27(m, 5H), 2.13(s, 3H), 2.27(s, 3H), 3.40(s, 2H), 6.70–7.33(m, 4H), 7.20(d, 1H, J = 8 Hz), 7.60(dd, 1H, J = 2, 8 Hz), 8.25(d, 1H, J = 2 Hz) |
| I-47 Route A | 0.87(d, 3H, J = 6 Hz), 1.25(d, 6H, J = 6 Hz), 1.67–3.33(m, 6H), 2.18(s, 3H), 3.45(s, 2H), 6.67–7.45(m, 4H), 7.25(d, 1H, J = 8 Hz), 7.65(dd, 1H, J = 2, 8 Hz), 8.32(d, 1H, J = 2 Hz) |
| I-48 Route A | 0.82(d, 3H, J = 6 Hz), 1.90–3.13(m, 5H), 2.13(s, 3H), 3.40(s, 2H), 7.07–7.43(m, 5H), 7.55(dd, 1H, J = 2, 8 Hz), 8.22(d, 1H, J = 2 Hz) |
| I-49 Route A | 0.80(d, 3H, J = 6 Hz), 1.63–3.00(m, 5H), 2.12(s, 3H), 3.38(s, 2H), 6.73–7.30(m, 4H), 7.17(d, 1H, J = 8 Hz), 7.57(dd, 1H, J = 2, 8 Hz), 8.20(d, 1H, J = 2 Hz) |
| I-50 Route A | 0.80(d, 3H, J = 6 Hz), 1.53–2.90(m, 5H), 2.12(s, 3H), 3.37(s, 2H), 6.83–7.17(m, 2H), 7.17(d, 1H, J = 8 Hz), 7.30–7.56(m, 2H), 7.56(dd, 1H, J = 2, 8 Hz), 8.20(d, 1H, J = 2 Hz) |
| I-51 Route A | 0.82(d, 3H, J = 6 Hz), 1.27(d, 6H, J = 6 Hz), 1.63–2.97(m, 5H), 2.12(s, 3H), 3.37(s, 2H), 4.20–4.67(m, 1H0, 6.43–6.77(m, 3H), 6.75–7.27(m, 1H), 7.15(d, 1H, J = 8 Hz), 7.55(dd, 1H, J = 8 Hz), 8.20(d, 1H, J = 2 Hz) |
| I-52 Route A | 0.82(d, 3H, J = 6 Hz), 1.62–3.12(m, 5H), 2.17(s, 3H), 3.42(s, 2H), 7.18–7.48(m, 2H), 7.20(d, 1H, J = 8 Hz), 7.60(dd, 1H, J = 2, 8 Hz), 7.75–8.10(m, 2H), 8.23(d, 1H, J = 2 Hz) |

TABLE 17

| compound no. | $^1$H-NMR (δ, ppm) |
|---|---|
| type of preparation method: Route A Route B-1 Route B-2 | |
| I-53 | 0.84(d, 3H, J = 7Hz), 2.08–2.27(m, 4H), |

TABLE 17-continued

| compound no. | ¹H-NMR (δ, ppm) |
|---|---|
| Route A | 2.17(s, 3H), 2.75(dd, 1H, J = 5, 14 Hz); 3.45(s, 2H), 6.62–6.70(m, 3H), 7.12(t, 1H, J = 8 Hz), 7.28(d, 1H, J = 8 Hz), 7.65(dd, 1H, J = 2, 8 Hz), 8.30(d, 1H, J = 2 Hz) |
| I-54 Route A | 0.82(d, 3H, J = 6 Hz), 1.50–3.08(m, 5H), 2.15(s, 3H), 3.42(s, 2H), 6.88(dd, 1H, J = 2, 8 Hz), 7.18(d, 1H, J = 2 Hz), 7.22(d, 1H, J = 8 Hz), 7.27(d, 1H, J = 8 Hz), 7.58(dd, 1H, J = 2, 8 Hz), 8.25(d, 1H, J = 2 Hz) |
| I-55 Route A | 0.83(d, 3H, J = 5Hz), 1.62–3.15(m, 5H), 2.15(s, 3H), 3.42(s, 2H), 6.92–7.38(m, 4H), 7.60(dd, 1H, J = 2, 8 Hz), 8.23(d, 1H, J = 2 Hz) |
| I-56 Route A | 0.82(d, 3H, J = 6 Hz), 1.72–3.25(m, 5H), 2.15(s, 3H), 3.42(s, 2H), 6.85–7.42(m, 4H), 7.58(dd, 1H, J = 2, 8 Hz), 8.23(d, 1H, J = 2 Hz) |
| I-57 Route A | 0.82(d, 3H, J = 6 Hz), 1.65–3.05(m, 5H), 2.13(s, 3H), 3.40(s, 2H), 6.93(d, 2H, J = 2 Hz), 7.05–7.22(m, 1H), 7.18(d, 1H, J = 8 Hz), 7.57(dd, 1H, J = 2, 8 Hz), 8.23(d, 1H, J = 2 Hz) |
| I-58 Route A | 0.83(d, 3H, J = 6 Hz), 1.77–2.90(m, 5H), 2.12(s, 3H), 3.38(s, 2H), 3.70(s, 6H), 6.23(s, 3H), 7.20(d, 1H, J = 8 Hz), 7.58(dd, 1H, J = 2, 8 Hz), 8.23(d, 1H, J = 2 Hz) |
| I-59 Route A | 0.80(d, 3H, J = 6 Hz), 1.85–2.92(m, 5H), 2.12(s, 3H), 3.37(s, 2H), 3.78(s, 3H), 6.70(d, 1H, 9 Hz), 6.92(dd, 1H, J = 2, 9 Hz), 7.07(d, 1H, J = 2 Hz), 7.18(d, 1H, J = 8 Hz), 7.57(dd, 1H, J = 2, 8 Hz), 8.22(d, 1H, J = 2 Hz) |
| I-60 Route A | 0.82(d, 3H, J = 6 Hz), 1.82–2.88(m, 5H), 2.13(s, 3H), 3.40(s, 2H), 4.32(bs, 1H), 6.78–7.37(m, 3H), 7.22(d, 1H, J = 8 Hz), 7.60(dd, 1H, J = 2, 8 Hz), 8.25(d, 1H, J = 2 Hz) |

TABLE 18

| compound no. | ¹H-NMR (δ, ppm) |
|---|---|
| type of preparation method: Route A Route B-1 Route B-2 | |
| I-61 Route A | 0.82(d, 3H, J = 6 Hz), 1.70–2.97(m, 5H), 2.12(s, 3H), 3.37(s, 2H), 6.83–7.33(m, 6H), 7.55(dd, 1H, J = 2, 8 Hz), 8.20(d, 1H, J = 2 Hz) |
| I-62 Route A | 0.82(d, 3H, J = 6 Hz), 1.75–3.05(m, 5H), 2.12(s, 3H), 3.42(s, 2H), 6.78–7.27(m, 4H), 7.22(d, 1H, J = 8 Hz), 7.60(dd, 1H, J = 2, 8 Hz), 8.27(d, 1H, J = 2 Hz) |
| I-63 Route A | 0.82(d, 3H, J = 6 Hz), 1.77–3.10(m, 5H), 2.15(s, 3H), 3.42(s, 2H), 7.17(d, 2H, J = 8 Hz), 7.22(d, 1H, J = 8 Hz), 7.48(d, 2H, J = 8 Hz), 7.58(dd, 1H, J = 2, 8 Hz), 8.27(d, 1H, J = 2 Hz) |
| I-64 Route A | 0.80(d, 3H, J = 6 Hz), 1.87–2.95(m, 5H), 2.15(s, 3H), 3.40(s, 2H), 6.58–7.25(m, 3H), 7.20(d, 1H, J = 8 Hz), 7.58(dd, 1H, J = 2, 8 Hz), 8.25(d, 1H, J = 2 Hz) |
| I-65 Route A | 0.80(d, 3H, J = 6 Hz), 1.53–2.93(m, 5H), 2.10(s, 3H), 3.35(s, 2H), 6.78–7.33(m, 5H), 7.50(dd, 1H, J = 2, 8 Hz), 8.13(d, 1H, J = 2 Hz) |
| I-66 Route A | 0.82(d, 3H, J = 7 Hz), 1.63–3.10(m, 5H), 2.13(s, 3H), 2.27(s, 3H), 3.38(s, 2H), 6.67–7.17(m, 4H), 7.13(d, 1H, J = 8 Hz), 7.53(dd, 1H, J = 2, 8 Hz), 8.18(d, 1H, J = 2 Hz) |
| I-67 Route A | 0.80(d, 3H, J = 6 Hz), 1.67–3.03(m, 5H), 2.13(s, 3H), 3.37(s, 2H), 7.07–7.43(m, 6H), 7.55(dd, 1H, J = 2, 8 Hz), 8.20(d, 1H, J = 2 Hz) |
| I-68 Route A | 0.82(d, 3H, J = 6 Hz), 1.60–2.93(m, 5H), 2.10(s, 3H), 3.37(s, 2H), 6.60–7.43(m, 10H), 7.55(dd, 1H, J = 2, 8 Hz), 8.22(d, 1H, J = 2 Hz) |
| I-69 | 0.82(d, 3H, J = 6 Hz), 1.27(s, 9H), |

TABLE 18-continued

| compound no. | ¹H-NMR (δ, ppm) |
|---|---|
| Route A | 1.53–3.00(m, 5H), 2.12(s, 3H), 3.38(s, 2H), 6.70–7.30(m, 5H), 7.55(dd, 1H, J = 2, 8 Hz), 8.20(d, 1H, J = 2 Hz) |
| I-70 Route A | 0.80(d, 3H, J = 6 Hz), 1.68–2.93(m, 5H), 2.13(s, 3H), 3.38(s, 2H), 6.67–7.05(m, 3H), 7.15(d, 1H, J = 8 Hz), 7.52(dd, 1H, J = 2, 8 Hz), 8.18(d, 1H, J = 2 Hz) |

TABLE 19

| compound no. | ¹H-NMR (δ, ppm) |
|---|---|
| type of preparation method: Route A Route B-1 Route B-2 | |
| I-71 Route A | 0.82(d, 3H, J = 6 Hz), 1.50–3.27(m, 5H), 2.17(s, 3H), 2.53(s, 3H), 3.42(s, 2H), 6.83–7.33(m, 3H.), 7.55(dd, 1H, J = 2, 8 Hz), 7.82(d, 1H, J = 8 Hz), 8.22(d, 1H, J = 2 Hz) |
| I-72 Route A | 0.82(d, 3H, J = 6 Hz), 1.58–3.02(m, 5H), 2.13(s, 3H), 3.38(s, 2H), 3.78(s, 3H), 6.42–6.75(m, 2H), 7.03–7.32(m, 2H), 7.53(dd, 1H, J = 2, 8 Hz), 8.20(d, 1H, J = 2 Hz) |
| I-73 Route A | 0.80(d, 3H, J = 6 Hz), 1.60–3.07(m, 5H), 2.12(s, 3H), 3.37(s, 2H), 3.93(bs, 1H), 6.50(dd, 1H, J = 2, 8 Hz), 6.70(d, 1H, J = 2 Hz), 7.08(d, 1H, J = 8 Hz), 7.17(d, 1H, J = 8 Hz), 7.53(dd, 1H, J = 2, 8 Hz), 8.18(d, 1H, J = 2 Hz) |
| I-74 Route A | 0.83(d, 3H, J = 6 Hz), 1.67–2.90(m, 5H), 2.13(s, 3H), 2.23(s, 6H), 3.38(s, 2H), 6.55–6.80(m, 3H), 7.15(d, 1H, J = 8 Hz), 7.55(dd, 1H, J = 2, 8 Hz), 8.20(d, 1H, J = 2 Hz) |
| I-75 Route A | 0.80(d, 3H, J = 6 Hz), 1.60–3.00(m, 5H), 2.17(s, 3H), 3.37(s, 2H), 6.50–7.30(m, 5H), 7.52(dd, 1H, J = 2, 8 Hz), 8.18(d, 1H, J = 2 Hz) |
| I-76 Route A | 0.83(d, 3H, J = 6 Hz), 1.70–3.10(m, 5H), 2.13(s, 3H), 3.38(s, 2H), 3.71(s, 3H), 6.50–6.80(m, 3H), 6.90–7.30(m, 2H), 7.55(dd, 1H, J = 2, 8 Hz), 8.20(d, 1H, J = 2 Hz) |
| I-77 Route A | 0.80(d, 3H, J = 6 Hz), 1.60–3.20(m, 5H), 2.13(s, 3H), 3.38(s, 2H), 5.10–5.50(m, 2H), 6.60–7.70(m, 7H), 8.24(d, 1H, J = 2 Hz) |
| I-78 Route A | 0.85(d, 3H, J = 6 Hz), 1.70–3.10(m, 5H), 2.12(s, 3H), 3.35(s, 2H), 6.80–7.90(m, 11H), 8.22(d, 1H, J = 2 Hz) |
| I-79 Route A | 0.83(d, 3H, J = 6 Hz), 1.80–3.10(m, 5H), 2.10(s, 3H), 3.35(s, 2H), 6.90–7.60(m, 11H), 8.12(d, 1H, J = 2 Hz) |

TABLE 20

| compound no. | ¹H-NMR (δ, ppm) |
|---|---|
| type of preparation method: Route A Route B-1 Route B-2 | |
| I-80 Route A | 0.82(d, 3H, J = 6 Hz), 1.80–2.90(m, 5H), 2.10(s, 3H), 2.16(s, 6H), 3.35(s, 2H), 6.60–7.20(m, 4H), 7.53(dd, 1H, J = 2, 8 Hz), 8.18(d, 1H, J = 2 Hz) |
| I-81 Route A | 0.82(d, 3H, J = 6 Hz), 1.60–3.20(m, 5H), 2.16(s, 3H), 3.43(s, 2H), 7.10–7.70(m, 5H), 8.24(d, 1H, J = 2 Hz) |
| I-82 | 0.80(d, 3H, J = 6 Hz), 1.70–2.90(m, 5H), |

TABLE 20-continued

| compound no. | $^1$H-NMR (δ, ppm) |
|---|---|
| Route A | 2.12(s, 3H), 2.27(s, 3H), 3.38(s, 2H), 6.70–7.30(m, 4H), 7.55(dd, 1H, J = 2, 8 Hz), 8.22(d, 1H, J = 2 Hz) |
| I-83 Route A | 0.80(d, 3H, J = 6 Hz), 1.68–2.95(m, 5H), 2.13(s, 3H), 3.40(s, 2H), 6.74–7.33(m, 4H), 7.56(dd, 1H, J = 2, 8 Hz), 8.23(d, 1H, J = 2 Hz) |
| I-84 Route A | 0.80(d, 3H, J = 6 Hz), 1.65–3.02(m, 5H), 2.13(s, 3H), 3.40(s, 2H), 6.75–7.42(m, 3H), 7.17(d, 1H, J = 8 Hz), 7.57(dd, 1H, J = 2, 8 Hz), 8.22(d, 1H, J = 2 Hz) |
| I-85 Route A | 0.80(d, 3H, J = 6 Hz), 1.58–2.95(m, 5H), 2.12(s, 3H), 3.38(s, 2H), 6.82(dd, 1H, J = 2, 8 Hz), 7.08–7.72(m, 4H), 8.22(d, 1H, J = 2 Hz) |
| I-86 Route A | 0.82(d, 3H, J = 6 Hz), 1.63–2.97(m, 5H), 2.13(s, 3H), 3.42(s, 2H), 6.67–7.40(m, 3H), 7.22(d, 1H, J = 8 Hz), 7.60(dd, 1H, J = 2, 8 Hz), 8.27(d, 1H, J = 2 Hz) |
| I-87 Route A | 0.82(d, 3H, J = 6 Hz), 1.77–3.27(m, 5H), 2.13(s, 3H), 3.40(s, 2H), 4.27(q, 2H, J = 8 Hz), 6.50-6.87(m, 3H), 7.00–7.37(m, 2H), 7.58(dd, 1H, J = 2, 8 Hz), 8.27(d, 1H, J = 2 Hz) |

TABLE 21

| compound no. | $^1$H-NMR (δ, ppm) |
|---|---|
| type of preparation method: Route A Route B-1 Route B-2 | |
| I-90 Route A | 0.83(d, 3H, J = 6 Hz), 1.55–2.42(m, 6H), 2.13(s, 3H), 2.52–3.02(m, 5H), 3.38(s, 2H), 6.63–7.18(m, 3H), 7.17(d, 1H, J = 8 Hz), 7.57(dd, 1H, J = 2, 8 Hz), 8.23(d, 1H, J = 2 Hz) |
| I-91 Route A | 0.80(d, 3H, J = 6 Hz), 1.25–2.88(m, 5H), 2.12(s, 3H), 3.37(s, 2H), 5.80(s, 2H), 6.28–6.82(m, 3H), 7.15(d, 1H, J = 8 Hz), 7.53(dd, 1H, J = 2, 8 Hz), 8.17(d, 1H, J = 2 Hz) |
| I-92 Route A | 0.85(d, 3H, J = 6 Hz), 1.80–3.10(m, 5H), 2.12(s, 3H), 3.35(s, 2H), 7.00–7.80(m, 9H), 8.23(d, 1H, J = 2 Hz) |

Table 22 shows the NMR data for a few 3-phenylpropylamine derivatives (IV) to be used as starting compounds for the preparation of compounds (I) by Route B-1 and Route B-2.

TABLE 22

| compound no. | $^1$H-NMR (δ, ppm) |
|---|---|
| IV-2 | 0.88(d, 3H, J = 6 Hz), 1.63(s, 1H), 1.72–3.32(m, 5H), 2.37(s, 3H), 6.93–7.43(m, 4H) |
| IV-3 | 0.87(d, 3H, J = 6 Hz), 1.40–3.23(m, 5H), 2.42(s, 3H), 4.38(s, 1H), 7.00(d, 2H, J = 8 Hz), 7.20(d, 2H, J = 8 Hz) |
| IV-4 | 0.87(d, 3H, J = 6 Hz), 1.17(s, 1H), 1.58–3.17(m, 5H), 2.37(s, 3H), 7.17–7.33(m, 3H) |

Formulation Example 1

Dusting Powder Formulation

The following ingredients were pulverized and blended for use as a dusting powder.

| | Parts by Weight |
|---|---|
| Compound (I-4) | 3 |
| Clay | 40 |
| Talc | 57 |

Formulation Example 2

Wettable Powder Formulation

The following ingredients were pulverized and blended into a wettable powder, and diluted with water for use.

| | Parts by weight |
|---|---|
| compound (I-12) | 50 |
| Lignin sulfonate | 5 |
| Alkylsulfonate | 3 |
| Diatomaceous earth | 42 |

Formulation Example 3

Granule Formulation

The following ingredients were uniformly blended, combined with water, kneaded and then processed and dried into granular form with an extruder-type granulator, to prepare granules.

| | Parts by weight |
|---|---|
| Compound (I-17) | 5 |
| Bentonite | 43 |
| Clay | 45 |
| Lignin sulfonate | 7 |

Formulation Example 4

Emulsifiable Concentrate Formulation

The following ingredients were uniformly blended and dissolved to prepare an emulsifiable concentrate.

| | Parts by Weight |
|---|---|
| Compound (I-4) | 20 |
| Polyoxyethylenealkyl allyl ether | 10 |
| Polyoxyethylene sorbitan monolaurate | 3 |
| Xylene | 67 |

Test Example 1

Test of Controlling Effect on Wheat Powdery Mildew

Seeslings of wheat (variety: "Abukumawase") at the first to second leaf period were cultivated using square plastic pots (size: 6.4 cm×6.4 cm). Such a wettable powder form as obtained in Formulation Example 2 was diluted and suspended with water to provide the prescribed concentration (500 mg/l), and was sprinkled onto wheat at a level of 100 liters/10 a (ares).

After air-drying the sprinkled leaves, a suspension of wheat powdery mildew spores taken from infected leaves was inoculated by spraying onto the air-dried sprinkled leaves. They were maintained under highly humid conditions at 20–24° C. for 24 h, and then supervised in a green house (temperature: 20–24° C., relative humidity: 20–70 RH). On the 9th to 14th days after inoculation, the infection degree was examined according to the following scale and the control value was calculated as shown below (Equation 1).

| (Examination Scale) | |
|---|---|
| Infection degree | Severity |
| 0 | No infection |
| 0.5 | Lesion area proportion: less than 1% |
| 1 | Lesion area proportion: 1% to less than 5% |
| 2 | Lesion area proportion: 5% to less than 10% |
| 3 | Lesion area proportion: 10% to less than 30% |
| 4 | Lesion area proportion: 30% to less than 50% |
| 5 | Lesion area proportion: 50% or more |

Control value (%)=(1−infection degree of treated zone/infection degree of untreated zone)×100     (Equation 1)

The results thus obtained above are shown in Tables 23–24 below.

TABLE 23

| compound no. | control value |
|---|---|
| I-1 | 83 |
| I-3 | 100 |
| I-4 | 100 |
| I-6 | 98 |
| I-7 | 100 |
| I-8 | 100 |
| I-9 | 100 |
| I-12 | 100 |
| I-13 | 80 |
| I-14 | 100 |
| I-17 | 98 |
| I-19 | 97 |
| I-23 | 100 |
| I-24 | 100 |
| I-25 | 100 |
| I-26 | 83 |
| I-27 | 98 |
| I-30 | 100 |
| I-34 | 80 |
| I-38 | 100 |
| I-39 | 100 |
| I-40 | 100 |
| I-41 | 88 |
| I-42 | 100 |
| I-43 | 100 |
| I-44 | 98 |
| I-45 | 100 |
| I-46 | 100 |
| I-47 | 100 |
| I-48 | 100 |
| I-49 | 100 |
| I-50 | 100 |

TABLE 24

| compound no. | control value |
|---|---|
| I-51 | 98 |
| I-52 | 90 |
| I-54 | 100 |
| I-55 | 98 |
| I-56 | 100 |
| I-57 | 100 |
| I-58 | 80 |
| I-59 | 100 |
| I-61 | 100 |
| I-63 | 100 |
| I-64 | 100 |
| I-65 | 100 |
| I-69 | 100 |
| I-70 | 100 |
| I-74 | 98 |
| I-75 | 70 |
| I-77 | 100 |
| I-79 | 80 |
| I-80 | 70 |
| I-81 | 100 |
| I-82 | 100 |
| I-90 | 70 |

Test Example 2

Test of Controlling Effect on Cucumber Powdery Mildew

Cucumber (variety: "Sagamihanpakufushinari") at the first to second leaf period was cultivated using square plastic pots (size: 6.4 cm×6.4 cm). Such a wettable powder form as obtained in Formulation Example 2 was diluted and suspended with water to provide the prescribed concentration (250 mg/l), and it was sprinkled onto the cucumber at a level of 100 liters/10
a. After air-drying the sprinkled leaves, spores taken from infected leaves were inoculated by dispersing with a brush onto the air-dried sprinkled leaves. An outbreak of the disease was allowed to occur in a glass green house (temperature: 20–24° C., relative humidity: 20–70 RH). On the 9th to 14th days after inoculation, the infection degree was examined according to the following scale and the control value was calculated as shown below (Equation 2).

| (Examination scale) | |
|---|---|
| Infection degree | Severity |
| 0 | No infection |
| 0.5 | Lesion area proportion: less than 5% |
| 1 | Lesion area proportion: 5% to less than 10% |
| 2 | Lesion area proportion: 10% to less than 30% |
| 3 | Lesion area proportion: 30% to less than 50% |
| 4 | Lesion area proportion: 50% to less than 70% |
| 5 | Lesion area proportion: 70% or more |

Control value (%)=(1−infection degree of treated zone/infection degree of untreated group)×100     (Equation 2)

The results thus obtained above are shown in Table 25 below.

TABLE 25

| compound no. | control value |
|---|---|
| I-4 | 98 |
| I-5 | 100 |
| I-6 | 100 |
| I-7 | 100 |
| I-8 | 100 |
| I-9 | 98 |
| I-12 | 100 |
| I-22 | 90 |
| I-25 | 98 |
| I-48 | 100 |
| I-49 | 100 |
| I-50 | 100 |
| I-54 | 100 |
| I-55 | 100 |
| I-57 | 100 |
| I-59 | 100 |
| I-65 | 100 |
| I-69 | 100 |
| I-78 | 100 |
| I-79 | 100 |
| I-80 | 100 |
| I-92 | 100 |

Test Example 3

Antifungal Activity Test against Various Pathogenic Fungi

In the test example, the antifungal activity of compounds of this invention was tested against various plant pathogenic fungi according to the method which will be descibed hereunder.

(Test Method)

Each 10 mg of a compound of the invention was weighed and dissolved in 1 ml of dimethyl sulfoxide. A 0.6 ml portion of the solution was added to 60 ml of PDA medium (potato-dextrose-agar medium) at about 60° C., and it was thoroughly mixed in a 100-ml Erlenmeyer flask and then poured into a petri dish to solidify to prepare a plate medium containing the compound of the invention at a final concentration of 100 mg/l.

Next, test fungi that had been precultured in a plate medium were punched out with a cork bowler of 4-mm diameter and seeded on the chemical-containing plate medium described above. After seeding, each fungi was cultured for 1–3 days at its optimum growth temperature (The optimum growth temperatures may be found, for example, by reference to the publication "LIST OF CULTURES, 1996 Microorganisms, 10th Edition, The Fermentation Research Institute (Foundation)." The growth of fungi was measured in terms of its colony diameter. In this way, the growth level of each of the fungi resulting on the chemical-containing plate medium was compared with the growth level of the same fungi in a chemical-free group, and the percent inhibition of hypha elongation was determined according to the following equation 3:

$$R = 100(dc - dt)/dc \quad \text{(Equation 3)}$$

wherein "R" represents hypha elongation inhibition (%), "dc" represents the colony diameter on non-treated plate medium, and "dt" represents the colony diameter on chemical-treated plate medium, respectively.

The results obtained as described above were evaluated at five levels according to the following scale.

Growth Inhibition

5: Hypha elongation inhibition of 90% or more
4: Hypha elongation inhibition of from 70% to less than 90%
3: Hypha elongation inhibition of from 40% to less than 70%
2: Hypha elongation inhibition of from 20% to less than 40%
1: Hypha elongation inhibition of less than 20%

The evaluation results thus obtained are shown in Table 26 below.

TABLE 26

| compound no. | test fungi | | | |
|---|---|---|---|---|
| | B. c. | M. f. | F. niv. | P. c. |
| I-4 | 5 | 5 | 5 | 5 |
| I-5 | 5 | 5 | 4 | 4 |
| I-6 | 5 | 5 | 5 | 4 |
| I-8 | 5 | 5 | 5 | 4 |
| I-9 | 5 | 5 | 5 | 5 |
| I-12 | 5 | 5 | 5 | 4 |
| I-13 | 5 | 5 | 5 | 4 |
| I-14 | 5 | 5 | 4 | 3 |
| I-16 | 4 | 5 | 4 | 5 |
| I-22 | 5 | 5 | 5 | 5 |

The following compounds exhibited level 5 inhibition against gray mold.
I-39, 40, 41, 42, 43, 44, 45, 46, 47, 48, 49, 50, 51, 54, 55, 56, 57, 58, 59, 61, 65, 66, 68, 69, 70, 72, 74, 75, 76, 77, 78, 79, 80, 81, 82, 90, 92

The meanings of the abbreviations in Table 26 above are as follows.
B.c.: *Botrytis cinerea* (Gray mold)
M.f.: *Monilinia fructicola* (Brown rot mold-peaches)
F.niv.: *Fusarium nivale* (Fusarium blight mold-wheat)
P.c.: *Phytophthora capsici* (Gray disease mold-cucumber)

Industrial Applicability

As explained above, this invention provides an N-heterocyclicmethylpropylamine derivative of formula (I):

(I)

[Chemical structure showing $R^2$-CH$_2$-N($R^3$)-CH$_2$-CH(CH$_3$)-CH$_2$-phenyl with $(R^1)_n$ substituent on phenyl ring]

or an acid addition salt thereof;
wherein $R^1$ represents at least one moiety selected from the group consisting of hydrogen, halogen, $C_1$–$C_6$ alkyl, $C_1$–$C_6$ alkenyl, $C_1$–$C_6$ halogenated alkyl, $C_1$–$C_6$ alkoxy, $C_1$–$C_6$ halogenated alkoxy, hydroxyl, cyano, nitro, phenyl optionally having a substituent on a ring thereof and phenoxy; n represents an integer of 0–5; when n is 2 or greater, each $R^1$ may be the same or different and two $R^1$ groups may be bonded together into a ring or crosslinked; $R^2$ represents a heterocycle containing at least one nitrogen atom as the hetero atom and optionally having a substituent on a ring thereof; and $R^3$ represents at least one moiety selected from the group consisting of hydrogen and $C_1$–$C_5$ alkyl.

The invention further provides a process for preparation comprising reductive amination between a 3-phenylpropionaldehyde derivative of formula (II) and a heterocyclicmethylamine derivative of formula (III) to obtain an N-heterocyclicmethylpropylamine derivative of formula (I):

(II)

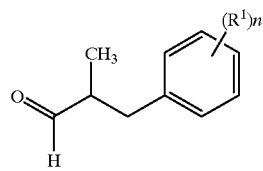

(III)

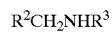

R²CH₂NHR³

(I)

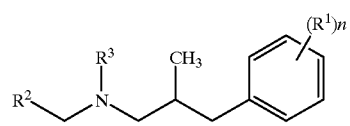

(in formulae (I), (II) and (III) $R^1$, $R^2$, $R^3$ and n are as previously defined).

The invention still further provides the following preparation processes.

A process for preparation comprising alkylation between a 3-phenylpropylamine derivative of formula (IV) and a heterocycle-methylating agent of formula (V) to obtain an N-heterocyclicmethylpropylamine derivative of formula (I):

(IV)

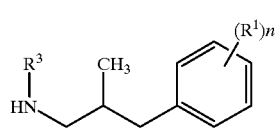

(V)

R²CH₂X (I)

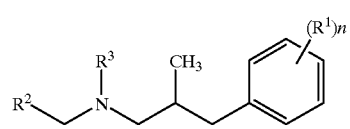

(in formulae (I), (IV) and (V) $R^1$, $R^2$, $R^3$ and n are as defined above, and X represents a leaving group).

A process for preparation comprising reductive amination between a 3-phenylpropylamine derivative of formula (IV) and a heterocyclicaldehyde derivative of formula (VI) to obtain an N-heterocyclicmethylpropylamine derivative of formula (I):

(IV)

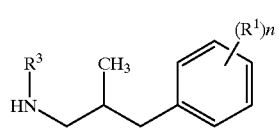

(VI)

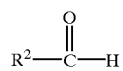

(I)

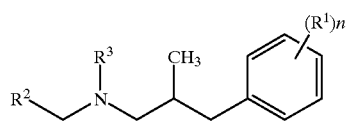

(in formulae (I), (IV) and (VI) $R^1$, $R^2$, $R^3$ and n are as previously defined).

The invention still further provides a fungicide containing an N-heterocyclicmethylpropylamine derivative of formula (I) or an acid addition salt thereof as the effective ingredient:

(I)

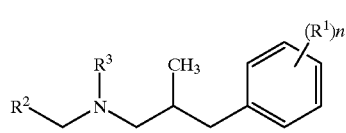

wherein $R^1$, $R^2$, $R^3$ and n are as previously defined.

The novel N-heterocyclicmethylpropylamine derivatives of the invention and their acid addition salts can most effectively be used as, e.g., such fungicides for farming and horticulture as stated above against a variety of pathogenic fungi.

What is claimed is:

1. An N-heterocyclicmethylpropylamine derivative of formula (I):

(I)

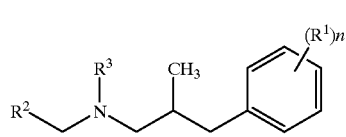

or an acid addition salt thereof;

wherein $R^1$ represents a moiety selected from the group consisting of hydrogen, halogen, $C_1$–$C_6$ alkyl, $C_1$–$C_6$ alkenyl, $C_1$–$C_6$ halogenated alkyl, $C_1$–$C_6$ alkoxy, $C_1$–$C_6$ halogenated alkoxy, hydroxyl, cyano, nitro, phenyl optionnally having a substituent on a ring thereof and phenoxy; n represents an integer of 0–5; when n is 2 or greater, each $R^1$ may be the same or different and two $R^1$ groups may be bonded together to form a ring selected from a group consisting of indane, 1,2-methylenedioxybenzene and naphthalene; $R^2$ represents a heterocycle selected from a group consisting of pyridine, pyrazine, pyrimidine, thiazole, oxazole, pyrazole and pyrrole, said heterocycle optionally having a substituent on a ring thereof; and $R^3$ represents a moiety selected from the group consisting of hydrogen and $C_1$–$C_5$ alkyl, with the proviso that the following compounds are excluded:

N-[3-(4-t-butylphenyl)-2-methylpropyl]-N-(t-butyl)-3-pyridylmethylamine,
N-[3-(4-t-butylphenyl)-2-methylpropyl]-N-butyl-3-pyridylmethylamine, and
N-[3-(4-t-butylphenyl)-2-methylpropyl]-N-methyl-3-pyridylmethylamine.

2. A fungicide compound containing as an effective ingredient, an N-heterocyclicmethylpropylamine derivative of formula (I):

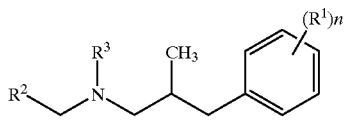

or an acid addition salt thereof;

wherein $R^1$ represents a moiety selected from the group consisting of hydrogen, halogen, $C_1$–$C_6$ alkyl, $C_1$–$C_6$ alkenyl, $C_1$–$C_6$ halogenated alkyl, $C_1$–$C_6$ alkoxy, $C_1$–$C_6$ halogenated alkoxy, hydroxyl, cyano, nitro, phenyl optionally having a substituent on a ring thereof and phenoxy; n represents an integer of 0–5; when n is 2 or greater, each $R^1$ may be the same or different and two $R^1$ groups may be bonded together to form a ring selected from a group consisting of indane, 1,2-methylenedioxybenzene and naphthalene; $R^2$ represents a heterocycle selected from a group consisting of pyridine, pyrazine, pyrimidine, thiazole, oxazole, pyrazole and pyrrole, said heterocycle optionally having a substituent on a thereof; and $R^3$ represents a moiety selected from the group consisting of hydrogen and $C_1$–$C_5$ alkyl, with the proviso that the following compounds are excluded:

N-[3-(4-t-butylphenyl)-2-methylpropyl]-N-(t-butyl)-3-pyridylmethylamine,

N-[3-(4-t-butylphenyl)-2-methylpropyl]-N-butyl-3-pyridylmethylamine, and

N-[3-(4-t-butylphenyl)-2-methylpropyl]-N-methyl-3-pyridylmethylamine.

\* \* \* \* \*